US011013535B2

(12) United States Patent
Carlson et al.

(10) Patent No.: US 11,013,535 B2
(45) Date of Patent: May 25, 2021

(54) VERTEBRAL FIXATION SYSTEM

(71) Applicant: Zimmer Spine, Inc., Edina, MN (US)

(72) Inventors: Daniel Carlson, Lulea (SE); Hugh Hestad, Edina, MN (US)

(73) Assignee: Zimmer Spine, Inc., Edina, MN (US)

(*) Notice: Subject to any disclaimer, the term of this patent is extended or adjusted under 35 U.S.C. 154(b) by 0 days.

(21) Appl. No.: 16/229,790

(22) Filed: Dec. 21, 2018

(65) Prior Publication Data

US 2019/0110820 A1 Apr. 18, 2019

Related U.S. Application Data

(63) Continuation of application No. 14/794,329, filed on Jul. 8, 2015, now Pat. No. 10,188,429, which is a continuation of application No. 13/687,220, filed on Nov. 28, 2012, now abandoned.

(51) Int. Cl.
*A61B 17/70* (2006.01)
*A61B 17/82* (2006.01)

(52) U.S. Cl.
CPC ...... *A61B 17/7029* (2013.01); *A61B 17/7049* (2013.01); *A61B 17/7053* (2013.01); *A61B 17/82* (2013.01)

(58) Field of Classification Search
CPC ........ A61B 17/70–7046; A61B 17/7049–7053
See application file for complete search history.

(56) References Cited

U.S. PATENT DOCUMENTS

| 2,049,361 A | 7/1936 | Johan |
| 4,244,083 A | 1/1981 | Aremka et al. |
| 4,570,618 A | 2/1986 | Wu |

(Continued)

FOREIGN PATENT DOCUMENTS

| EP | 1205152 B1 | 9/2004 |
| EP | 2052689 A1 | 4/2009 |

(Continued)

OTHER PUBLICATIONS

"U.S. Appl. No. 13/687,220, Final Office Action dated May 8, 2015", 10 pgs.

(Continued)

*Primary Examiner* — Eduardo C Robert
*Assistant Examiner* — Steven J Cotroneo
(74) *Attorney, Agent, or Firm* — Schwegman Lundberg & Woessner, P.A.

(57) ABSTRACT

A vertebral fixing system having a flexible elongated member, a connecting part, and an anchor, where the anchor may engage a bone structure (e.g., a vertebra) through an opening of the connecting part and the flexible elongated member may connect to the connecting part. In some cases, the vertebral fixing system may include a tightening part configured to apply a tension to the elongated member and/or secure the elongated member with respect to the connecting part. The vertebral fixing system may be configured to receive a rod and may be capable of connecting thereto. The connecting part may have a plurality of connecting members, where at least one of the connecting members includes an opening for receiving the anchor and at least one of the connecting members connects to the elongated member.

19 Claims, 20 Drawing Sheets

(56) References Cited

U.S. PATENT DOCUMENTS

| | | | |
|---|---|---|---|
| 5,030,220 | A | 7/1991 | Howland |
| 5,172,455 | A * | 12/1992 | Johnson .............. A44B 11/14 |
| | | | 24/170 |
| 5,304,178 | A | 4/1994 | Stahurski |
| 5,356,412 | A * | 10/1994 | Golds ............. A61B 17/1327 |
| | | | 24/170 |
| 5,772,663 | A | 6/1998 | Whiteside et al. |
| RE36,221 | E | 6/1999 | Breard et al. |
| 5,928,237 | A * | 7/1999 | Farris ............. A61B 17/8861 |
| | | | 606/103 |
| 5,935,133 | A | 8/1999 | Wagner et al. |
| 5,964,769 | A | 10/1999 | Wagner et al. |
| 6,053,921 | A | 4/2000 | Wagner et al. |
| 6,086,590 | A | 7/2000 | Margulies et al. |
| 6,179,838 | B1 | 1/2001 | Fiz |
| 6,277,120 | B1 * | 8/2001 | Lawson ............ A61B 17/7053 |
| | | | 606/263 |
| 6,299,613 | B1 | 10/2001 | Ogilvie et al. |
| 6,309,390 | B1 | 10/2001 | Le Couedic et al. |
| 6,355,039 | B1 | 3/2002 | Troussel et al. |
| 6,391,030 | B1 | 5/2002 | Wagner et al. |
| 6,514,255 | B1 * | 2/2003 | Ferree ............. A61B 17/7053 |
| | | | 606/103 |
| 6,547,790 | B2 | 4/2003 | Harkey, III et al. |
| 6,605,091 | B1 | 8/2003 | Iwanski |
| 6,682,533 | B1 | 1/2004 | Dinsdale et al. |
| 6,695,852 | B2 | 2/2004 | Gleason |
| 7,377,472 | B2 | 5/2008 | Brown et al. |
| 7,481,828 | B2 | 1/2009 | Mazda et al. |
| 7,611,352 | B2 | 11/2009 | Abels et al. |
| 7,909,853 | B2 * | 3/2011 | Zucherman ........ A61B 17/7068 |
| | | | 606/249 |
| 7,959,654 | B2 | 6/2011 | Mazda et al. |
| 8,128,635 | B2 | 3/2012 | Belliard et al. |
| 8,162,946 | B2 | 4/2012 | Baccelli et al. |
| 8,172,843 | B2 | 5/2012 | Baccelli et al. |
| 8,267,943 | B2 * | 9/2012 | Ferree ............ A61B 17/06166 |
| | | | 606/139 |
| 9,345,518 | B2 * | 5/2016 | Larroque-Lahitette ............. A61B 17/7002 |
| 10,188,429 | B2 | 1/2019 | Carlson et al. |
| 2001/0027319 | A1 | 10/2001 | Ferree |
| 2002/0116013 | A1 | 8/2002 | Gleason et al. |
| 2002/0187452 | A1 | 12/2002 | Abels et al. |
| 2004/0157186 | A1 | 8/2004 | Abels et al. |
| 2005/0245929 | A1 * | 11/2005 | Winslow ........... A61B 17/7067 |
| | | | 606/249 |
| 2005/0273983 | A1 * | 12/2005 | Mattchen ............. F16G 11/101 |
| | | | 24/136 R |
| 2006/0172247 | A1 | 8/2006 | Abels et al. |
| 2006/0195088 | A1 | 8/2006 | Sacher et al. |
| 2006/0217713 | A1 | 9/2006 | Serhan et al. |
| 2007/0276500 | A1 * | 11/2007 | Zucherman ........ A61B 17/7053 |
| | | | 623/17.16 |
| 2008/0033436 | A1 * | 2/2008 | Song ................ A61B 17/7055 |
| | | | 606/86 A |
| 2009/0093820 | A1 * | 4/2009 | Trieu ................. A61B 17/701 |
| | | | 606/103 |
| 2009/0105715 | A1 * | 4/2009 | Belliard ............. A61B 17/707 |
| | | | 606/103 |
| 2009/0138048 | A1 | 5/2009 | Baccelli et al. |
| 2009/0177233 | A1 | 7/2009 | Malek |
| 2009/0182379 | A1 | 7/2009 | Baccelli et al. |
| 2009/0248077 | A1 * | 10/2009 | Johns ................ A61B 17/7026 |
| | | | 606/246 |
| 2009/0270920 | A1 * | 10/2009 | Douget ............. A61B 17/7055 |
| | | | 606/254 |
| 2009/0326585 | A1 * | 12/2009 | Baccelli ............. A61B 17/707 |
| | | | 606/263 |
| 2010/0137913 | A1 | 6/2010 | Khatchadourian et al. |
| 2010/0249845 | A1 | 9/2010 | Meunier et al. |
| 2011/0034956 | A1 | 2/2011 | Mazda et al. |
| 2011/0093015 | A1 | 4/2011 | Ramsay et al. |
| 2011/0112581 | A1 | 5/2011 | Clement |
| 2011/0238118 | A1 | 9/2011 | Baccelli et al. |
| 2011/0238125 | A1 | 9/2011 | Baccelli et al. |
| 2011/0245875 | A1 | 10/2011 | Karim |
| 2011/0301644 | A1 | 12/2011 | Belliard |
| 2012/0022591 | A1 | 1/2012 | Baccelli et al. |
| 2012/0022592 | A1 | 1/2012 | Belliard |
| 2012/0059377 | A1 | 3/2012 | Belliard |
| 2012/0130373 | A1 | 5/2012 | Larroque-Lahitette |
| 2012/0136394 | A1 | 5/2012 | Calvosa et al. |
| 2012/0245638 | A1 | 9/2012 | Druma |
| 2012/0259367 | A1 | 10/2012 | Lange |
| 2012/0283781 | A1 | 11/2012 | Arnin |
| 2012/0303065 | A1 | 11/2012 | Larroque-Iahitette et al. |
| 2013/0023878 | A1 * | 1/2013 | Belliard ............ A61B 17/7053 |
| | | | 606/74 |
| 2013/0041410 | A1 | 2/2013 | Hestad et al. |
| 2013/0123851 | A1 * | 5/2013 | Seme ................... A61B 17/70 |
| | | | 606/250 |
| 2013/0123853 | A1 | 5/2013 | Seme et al. |
| 2013/0282064 | A1 | 10/2013 | Arnin |
| 2014/0094850 | A1 * | 4/2014 | Clement ........... A61B 17/7001 |
| | | | 606/263 |
| 2014/0148854 | A1 | 5/2014 | Carlson et al. |
| 2014/0236234 | A1 * | 8/2014 | Kroll ................ A61B 17/7016 |
| | | | 606/264 |
| 2015/0305780 | A1 | 10/2015 | Carlson et al. |

FOREIGN PATENT DOCUMENTS

| | | |
|---|---|---|
| EP | 2138122 A1 | 12/2009 |
| FR | 2749155 A1 | 12/1997 |
| WO | WO-0154599 A1 | 8/2001 |
| WO | WO-0209604 A1 | 2/2002 |
| WO | WO-0217803 A2 | 3/2002 |
| WO | WO-2009144663 A1 | 12/2009 |
| WO | WO-2011012690 A1 | 2/2011 |

OTHER PUBLICATIONS

"U.S. Appl. No. 13/687,220, Non Final Office Action dated Oct. 22, 2014", 27 pgs.

"U.S. Appl. No. 13/687,220, Response filed Jan. 12, 2015 to Non Final Office Action dated Oct. 22, 2014", 11 pgs.

"U.S. Appl. No. 13/687,220, Response filed Sep. 3, 2014 to Restriction Requirement dated Jul. 3, 2014", 6 pgs.

"U.S. Appl. No. 13/687,220, Restriction Requirement dated Jul. 3, 2014", 8 pgs.

"U.S. Appl. No. 14/794,329, Final Office Action dated Aug. 23, 2017", 12 pgs.

"U.S. Appl. No. 14/794,329, Non Final Office Action dated Feb. 7, 2018", 13 pgs.

"U.S. Appl. No. 14/794,329, Non Final Office Action dated Feb. 8, 2017", 10 pgs.

"U.S. Appl. No. 14/794,329, Notice of Allowance dated Sep. 25, 2018", 9 pgs.

"U.S. Appl. No. 14/794,329, Response filed Jan. 11, 2017 to Restriction Requirement dated Nov. 23, 2016", 8 pgs.

"U.S. Appl. No. 14/794,329, Response filed May 4, 2018 to Non Final Office Action dated Feb. 7, 2018", 14 pgs.

"U.S. Appl. No. 14/794,329, Response filed May 8, 2017 to Non Final Office Action dated Feb. 8, 2017", 14 pgs.

"U.S. Appl. No. 14/794,329, Response filed Nov. 7, 2017 to Final Office Action dated Aug. 23, 2017", 16 pgs.

"U.S. Appl. No. 14/794,329, Restriction Requirement dated Nov. 23, 2016", 6 pgs.

"European Application Serial No. 13194726.9, Communication Pursuant to Article 94(3) EPC dated Apr. 12, 2017", 7 pgs.

"European Application Serial No. 13194726.9, Communication Pursuant to Article 94(3) EPC dated Oct. 24, 2016", 5 pgs.

"European Application Serial No. 13194726.9, Communication Pursuant to Article 94(3) EPC dated Dec. 5, 2017", 5 pgs.

"European Application Serial No. 13194726.9, Examination Notification Art. 94(3) dated Feb. 2, 2016", 5 pgs.

(56) References Cited

OTHER PUBLICATIONS

"European Application Serial No. 13194726.9, Examination Notification Art. 94(3) dated May 26, 2015", 6 pgs.
"European Application Serial No. 13194726.9, Extended European Search Report dated Jun. 3, 2014", 11 pgs.
"European Application Serial No. 13194726.9, Partial European Search Report dated Mar. 21, 2014", 5 pgs.
"European Application Serial No. 13194726.9, Response filed Jan. 5, 2015 to Extended European Search Report dated Jun. 3, 2014", 10 pgs.
"European Application Serial No. 13194726.9, Response filed Mar. 3, 2017 to Examination Notification Art. 94(3) dated Oct. 24, 2016", 6 pgs.
"European Application Serial No. 13194726.9, Response filed Apr. 11, 2018 to Communication Pursuant to Article 94(3) EPC dated Dec. 5, 2017", 62 pgs.
"European Application Serial No. 13194726.9, Response filed Aug. 11, 2016 to Examination Notification Art. 94(3) dated Feb. 2, 2016", 5 pgs.
"European Application Serial No. 13194726.9, Response filed Aug. 21, 2017 to Communication Pursuant to Article 94(3) EPC dated Apr. 12, 2017", 11 pgs.
"European Application Serial No. 13194726.9, Response filed Oct. 5, 2015 to Examination Notification Art. 94(3) dated May 26, 2015", 19 pgs.
"Merriam-Webster", Pliable, Merriam-webster.com/dictionary/pliable.

\* cited by examiner

VERTEBRAL FIXATION SYSTEM

CROSS-REFERENCE TO RELATED APPLICATIONS

This application is a continuation of U.S. patent application Ser. No. 14/794,329, filed on Jul. 8, 2015, now issued as U.S. Pat. No. 10,188,429 which is a continuation of U.S. patent application Ser. No. 13/687,220, filed on Nov. 28, 2012, the contents of which are fully incorporated herein by reference.

TECHNICAL FIELD

The disclosure is directed to vertebral fixing systems. More particularly, the disclosure is directed to vertebral fixing systems suitable for being mounted on a vertebra.

BACKGROUND

The spine is constituted by superposed vertebrae that are normally in alignment along a vertical axis going from the lumbar vertebrae to the cervical vertebrae, each vertebrae presenting a posterior wall from which there projects a spinous process and two sides having walls from which there project the ribs and/or transverse processes. When the spine of an individual presents abnormal curvature, the vertebrae are inclined relative to one another and/or relative to the vertebral axis. For example, the sides of the vertebrae situated on one side may be moved closer together forming a concave side, whereas the sides of the vertebrae on the other side may be spaced apart from one another and form a convex side.

In order to straighten the spinal column, a spinal stabilization system may be surgically installed along a vertebral segment. In order to keep the vertebrae in a desired relative position, known devices have screws that are inserted in the vertebrae and/or hooks that are inserted along the inside wall of the vertebral canal, and rods that are for interconnecting the screws and/or the hooks.

SUMMARY

The disclosure is directed to several alternative or complementary designs, materials, and methods of using medical device structures and assemblies. Although it is noted that conventional vertebral fixing systems and similar devices exist, there exists a need for improvement on those devices.

Accordingly, one illustrative embodiment of the disclosure may include a vertebral fixing system having an elongated member (e.g., a flexible elongated member), a connecting part, and an anchor, where the anchor may engage a bone structure through an opening in the connecting part and the elongated member may connect to the connecting part. The elongated member may be flexible and may connect to the connecting part in any manner. For example, the elongated member may be looped through an opening in the connecting part (e.g., the opening through which the anchor may be inserted and/or through a different opening), the elongated member may be mechanically fixed to the connecting part through gluing, applying pressure, clamping, riveting, sewing, or other mechanical fixation or fastening techniques, and/or the elongated member may be connected to the connecting part in any other manner, as desired.

In some cases, the connecting part may have a first connecting member with an opening and a second connecting member with an opening, where the bone anchor may be inserted through the opening of the first connecting member and/or the opening of the second connecting member to engage a bone structure. Illustratively, the first connecting member and the second connecting member may be movable with respect to the other of the first connecting member and the second connecting member. Alternatively, the first connecting member and the second connecting member may be unitarily formed and substantially fixed with respect to the other of the first connecting member and the second connecting member. Each, or at least one, of the connecting members may be connected to the elongated member(s).

In some illustrative instances, the vertebral fixing system may include a tightening part. The tightening part may be in adjustable connection with the elongated member and may be configured to secure the elongated member with respect to the connecting part. In an illustrative example, the elongated member connected to the connecting part may be wrapped around a bone structure or other structure and inserted into the tightening part, where the tightening part may be used to retain and/or apply a tension in and/or to the inserted elongated member and/or secure the elongated member in a position with respect to the connecting part.

In some instances, the vertebral fixing system may be used in a method of manipulating spinal anatomy. For example, the anchor of the vertebral fixing system may be inserted through an opening of the connecting part and connected to a first portion of the spinal anatomy. In the example, the elongated member connected to the connecting part may be extended around a second portion of the spinal anatomy and inserted into a tightening member or part. Then, the elongated member extending between the connecting part and the second portion of the spinal anatomy may be tensioned and locked into a position with the tightening member to maintain a tension in the elongated member.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
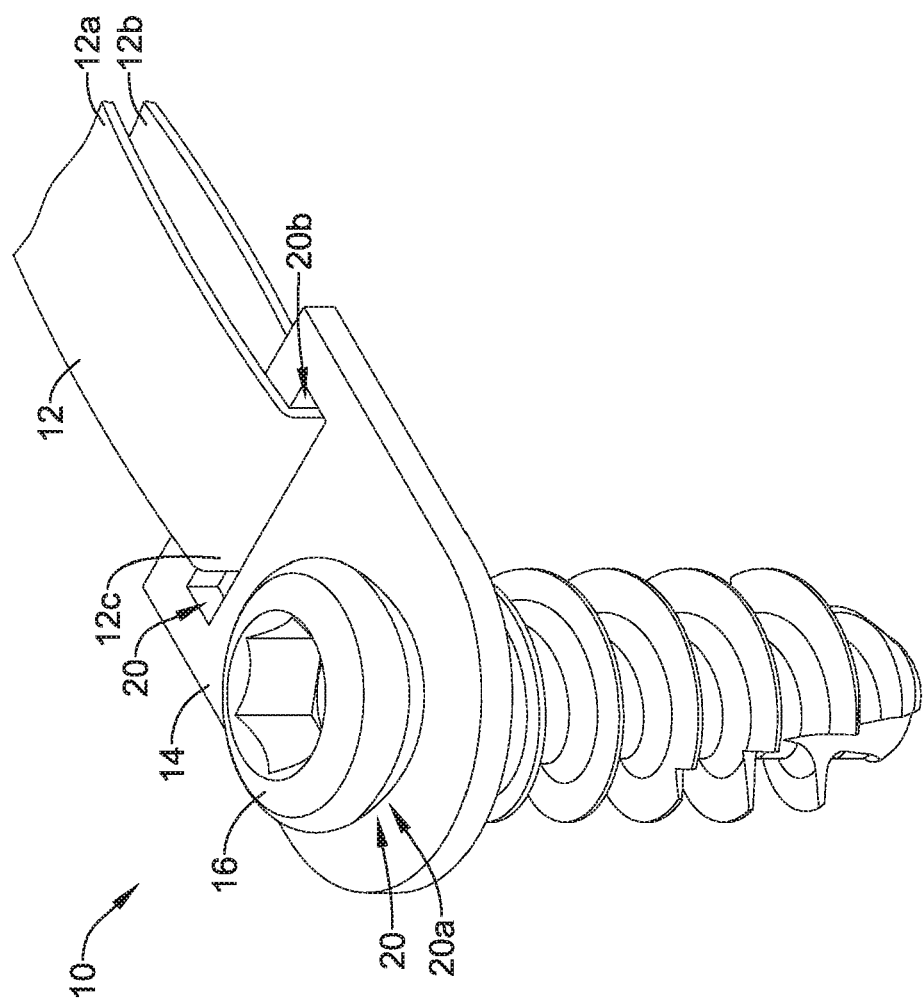
FIG. 1 is a schematic perspective view of an illustrative vertebral fixing system according to an aspect of the disclosure.
Figure 2:
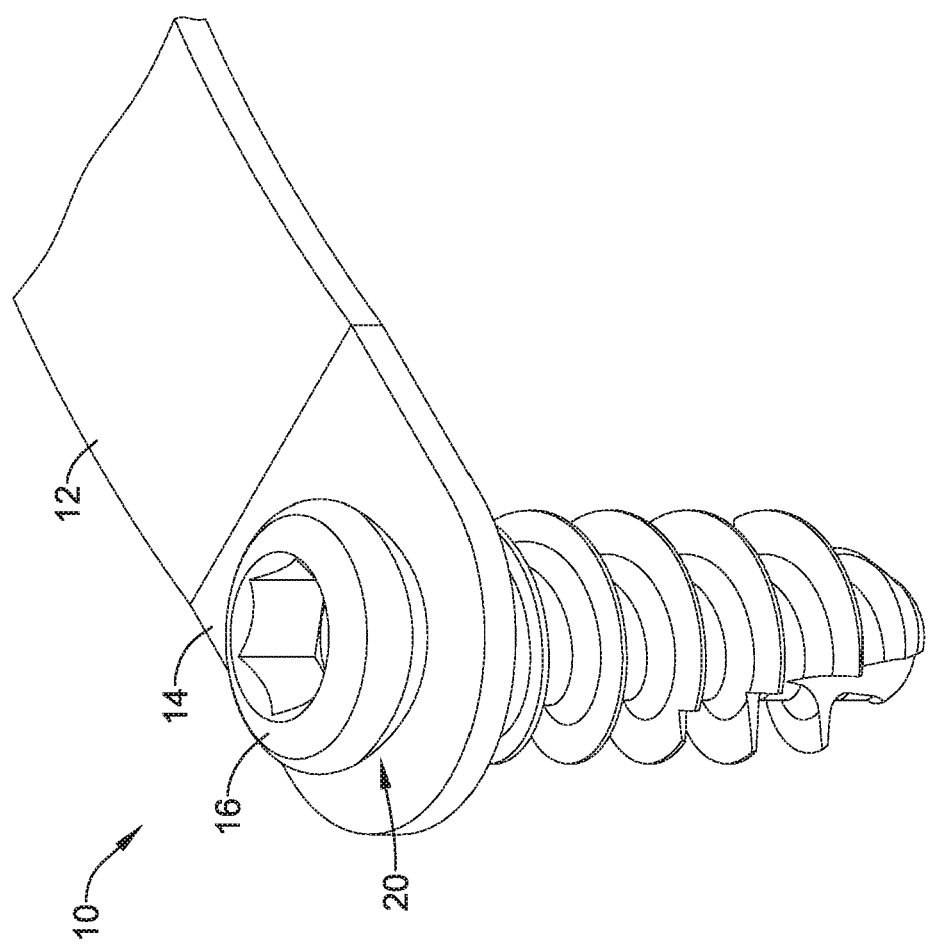
FIG. 2 is a schematic perspective view of an illustrative vertebral fixing system according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the proximal end (i.e., trailing end) of an object is the end that is closest to the individual or instrument inserting the object during a medical procedure and the distal end (i.e., leading end) of an object is the end that is farthest from the individual or instrument inserting the object during a medical procedure.

As used herein, any numerical or other order designations of elements (e.g., first, second, third, a, b, c, etc.) are used for descriptive purposes to improve the clarity of the description of the disclosure and differentiate between similar disclosed features. These numerical indications, unless expressly indicated, are not used for any limiting purposes.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Turning to the figures, FIGS. 1-15 depict illustrative vertebral fixing systems 10. Generally, vertebral fixing systems 10 may include an elongated member 12 (e.g., a flexible elongated member or ligature, as shown in FIGS. 1-15, or an inflexible elongated member), a connecting part 14, an anchor 16 (e.g., a bone anchor, a bone screw, or other fastener or anchor), and/or a tightening part 18. In some instances, illustrative vertebral fixing systems 10 may be configured to engage a bone (e.g., a vertebra, a rib, or other bone structure) via the bone anchor 16, the elongated member 12, and/or any other feature, where the elongated member 12 may extend from the connecting part 14 and may be configured to be wrapped around at least a portion of a bone structure and inserted into the tightening part 18.

In some illustrative cases, the connecting part 14 may be configured in the shape of a grommet or washer and may include an opening(s) 20 through which objects may be received or inserted (e.g., a first opening 20a and a second opening 20b, as shown in FIG. 1, or any other number of openings 20). For example, in some instances the connecting part 14 may be a flat member having an upper surface, a lower surface opposite the upper surface, and one or more, or a plurality of openings 20 extending through the connecting part 14 from the upper surface to the lower surface. The lower surface of the connecting part 14 may be configured to face and/or contact a bony structure of a vertebra.

The connecting part 14 may devoid of any structure (e.g., an elongate channel) for coupling the connecting part 14 to a spinal rod and thus not be configured to be coupled to an elongate spinal rod.

Illustratively, the opening(s) 20 may be sized and/or otherwise configured to receive the threaded anchor 16 and/or the elongated member 12. For example, the opening 20 may be sized such that the threaded anchor 16 may be inserted through the opening 20 to engage a vertebra and to position the connecting part 14 with respect to the vertebra (e.g., with the lower surface bearing against a bony structure of the vertebra). In some instances, the anchor 16 may be removable from the connecting part 14, or the anchor 16 may be configured to be retained with the connecting part 14. For example, in some instances the anchor 16 may be pre-assembled with the connecting part 14 during manufacture, and provided as an assembly during a surgical procedure. In some such instances, the anchor 16 may be rotatable relative to the connecting part 14 but not removable from the connecting part 14. In the example, once the anchor 16 is inserted through the opening 20 and engaging the vertebra, connecting part 14 may be in a fixed position relative to the vertebra or the connecting part 14 may be in an adjustable position with respect to the vertebra.

The connecting part 14 may be made of any material. For example, the connecting part 14 may be made of a metal material, a polymer material, or any other similar or dissimilar material, as desired. The opening(s) 20 in the material of the connecting part 14 may be formed through any technique. For example, the opening(s) 20 may be punched out, drilled out, or milled out of the material of the connecting part 14, molded into the material of the connecting part 14, and/or developed in any other similar or dissimilar manner.

In some instances, the elongated member 12 (e.g., a flexible elongated member) may have a first portion 12a, a second portion 12b, and a third portion 12c (e.g., an intermediate portion) extending between the first portion 12a of the elongated member 12 and the second portion 12b of the elongated member 12, where the first portion 12a and the second portion 12b of the elongated member 12 may be end portions. Illustratively, the first portion 12a, the second portion 12b, and/or the third portion 12c of the elongated member 12 may be configured to engage the connecting part 14 in any manner. For example, the elongated member 12 may mechanically engage the connecting part(s) 14 (see FIGS. 2 and 3), the elongated member 12 may be threaded through the opening 20 (e.g., the second opening 20b, as shown in FIG. 1) of the connecting part 14, or the elongated member 12 may engage the connecting part in any other manner, as desired. In some instances, the second portion 12b may be attached (e.g., stitched, glued, riveted, etc.) to the first portion 12a, forming a loop portion with the third portion 12c extending through the opening 20b, with only the first portion 12a being a free end portion extending from the connecting part 14. In other instances, the first portion 12a and the second portion 12b may both be free end portions extending from the connecting part 14. Example mechanical engagements between the connecting part 14 and the elongated member 12 include, but are not limited to, welded engagements, glued engagements, press-fit or crimped engagements, clamped engagements, riveted engagements, etc.

As discussed, the connecting part 14 may include the first opening 20a and the second opening 20b. In such instances, the anchor 16, illustratively, may be configured to be inserted through the first opening 20a to engage a portion of an anatomy (e.g., a bone) accessible through the first opening 20a. The second opening 20b may facilitate the connection between the connecting part 14 and the elongated member 12, as shown in FIG. 1. For example, the elongated member 12 may connect to the connecting part 14 via insertion through the second opening 20b of the connecting part 14 and wrapping the elongated member around the connecting part 14. The second opening 20b may be arranged laterally from the first opening 20a, such that the second opening 20b is located within a portion of the connecting part 14 extending away from the anchor 16.

Figure 3A:
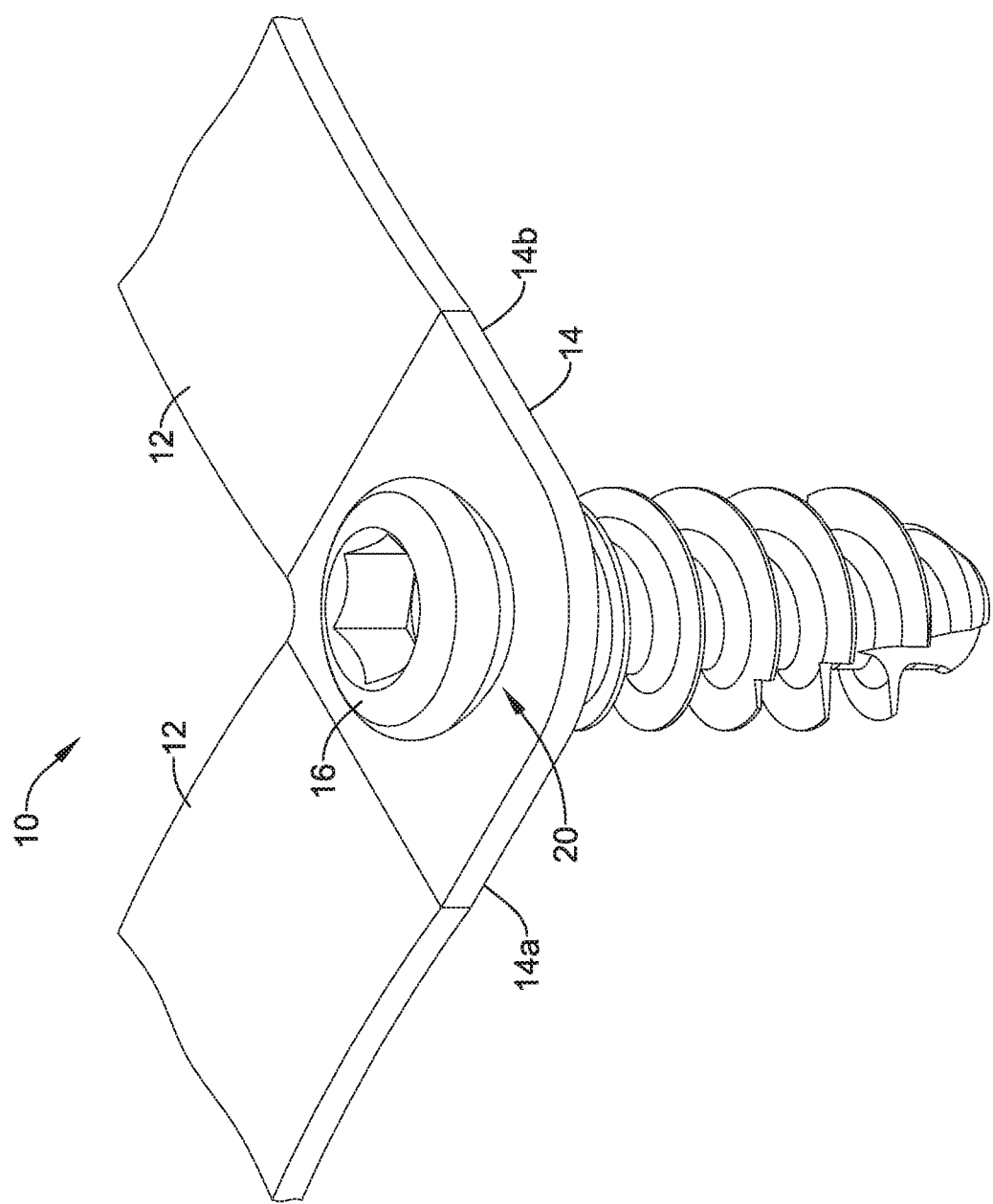
FIG. 3A is a schematic perspective view of an illustrative vertebral fixing system according to an aspect of the disclosure.
Figure 3B:
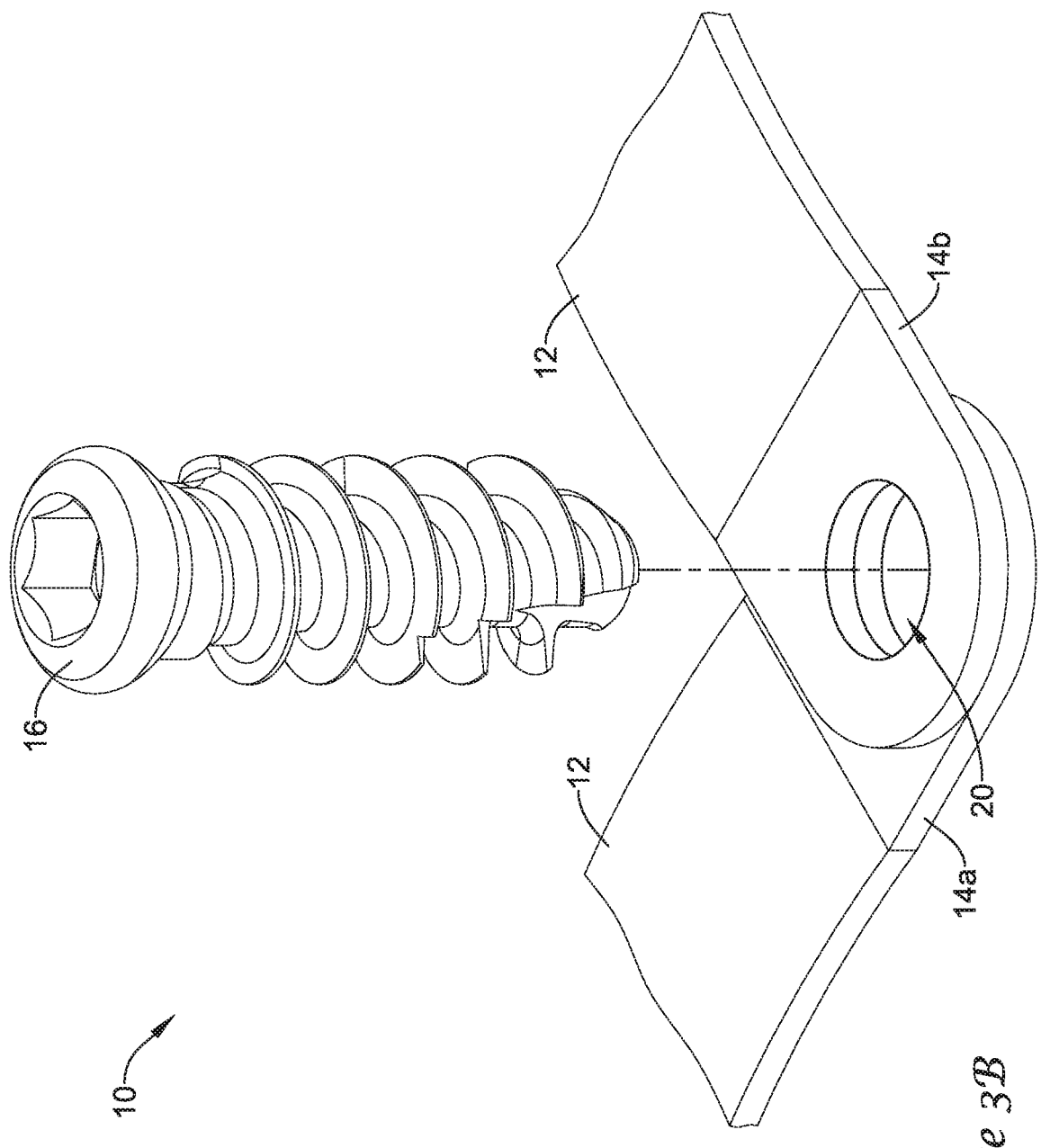
FIG. 3B is a schematic perspective partially exploded view of an illustrative vertebral fixing system according to an aspect of the disclosure.

In some instances, the connecting part 14 may include a first connecting member 14a and a second connecting member 14b having an opening 20, as shown in FIGS. 3A and 3B. When engaged by an anchor 16 and/or when separate from the anchor 16, the first connecting member 14a and the second connecting member 14b of the connecting part 14 may be fixed relative to one another (e.g., unitarily formed, as shown in FIG. 3A, or fixed relative to one another in any other manner). Alternatively, as shown in FIG. 3B, the first connecting member 14a of the connecting part 14 and/or the second connecting member 14b of the connecting part 14 may be configured to be adjusted relative to one another (e.g., pivoted about an anchor 16 received through the opening 20 of the first connecting member 14a and/or the opening of the second connecting member 14b, and/or otherwise movable with respect to the other connecting member 14a, 14b).

As illustrated in FIG. 3A, the first connecting member 14a and the second connecting member 14b may be unitarily configured and have a single opening 20 configured to receive the anchor 16. Alternatively, as shown in FIG. 3B, each of the first connecting member 14a and the second connecting member 14b may be separately configured and may have separate openings 20 configured to receive the anchor 16. The openings 20 of the first connecting member 14a and the second connecting member 14b may be positioned and/or aligned with respect to one another such that the anchor 16 may be inserted through the opening 20 of the first connecting member 14a and the opening 20 of the second connecting member 14b to engage a bone (e.g., a vertebra, a rid, or other bone structure).

The elongated member 12 may engage the first connecting member 14a and/or the second connecting member 14b in any manner. In some instances, an elongated member 12 may extend from each of the first connecting member 14a and the second connecting member 14b. For example, each of the first connecting member 14a and the second connecting member 14b may include a first opening 20a and a second opening 20b, where an elongated member 12 may be threaded through each of the second openings 20b of the respective first connecting member 14a and the second connecting member 14b or a single elongated member 12 may be threaded through both of the second openings 20b of the respective first connecting member 14a and the second connecting member 14b. Alternatively, an elongated member 12 may mechanically engage each of the first connecting member 14a and the second connecting member 14b or a single elongated member 12 may mechanically engage both of the second openings 20b of the respective first connecting member 14a and the second connecting member 14b.

The tightening part 18 or clamping part may be any configuration capable of engaging the first portion 12a of the elongated member 12, the second portion 12b of the elongated member 12, and/or the third portion 12c of the elongated member 12 to secure the elongated member 12 with respect to the connecting part 14, the anchor 16, and/or any other feature, as desired. For example, the tightening part 18 may have a configuration that includes a one-way catch mechanism 22 (e.g., a gear, zip-tie head), a release 24 to allow for adjustment of the elongated member 12 with respect to a bone (e.g., a vertebra) or other piece of human anatomy, and/or any other engaging and/or tightening features, as desired. Alternatively, or in addition, in some instances, the tightening part 18 may be configured to receive and engage a portion of the elongated member 12 (e.g., the second portion 12b of the elongated member 12) that has been wrapped and/or extended around a bone (e.g., a vertebra, a rib, or other bone) to substantially secure the portion of the elongated member 12 with respect to the connecting part 14, the anchor 16, the bone, and/or the other feature.

The tightening part 18 may be made of any material. For example, the tightening part 18 may be made of a metal material, a polymer material, or any other similar or dissimilar material, as desired.

Figure 4:
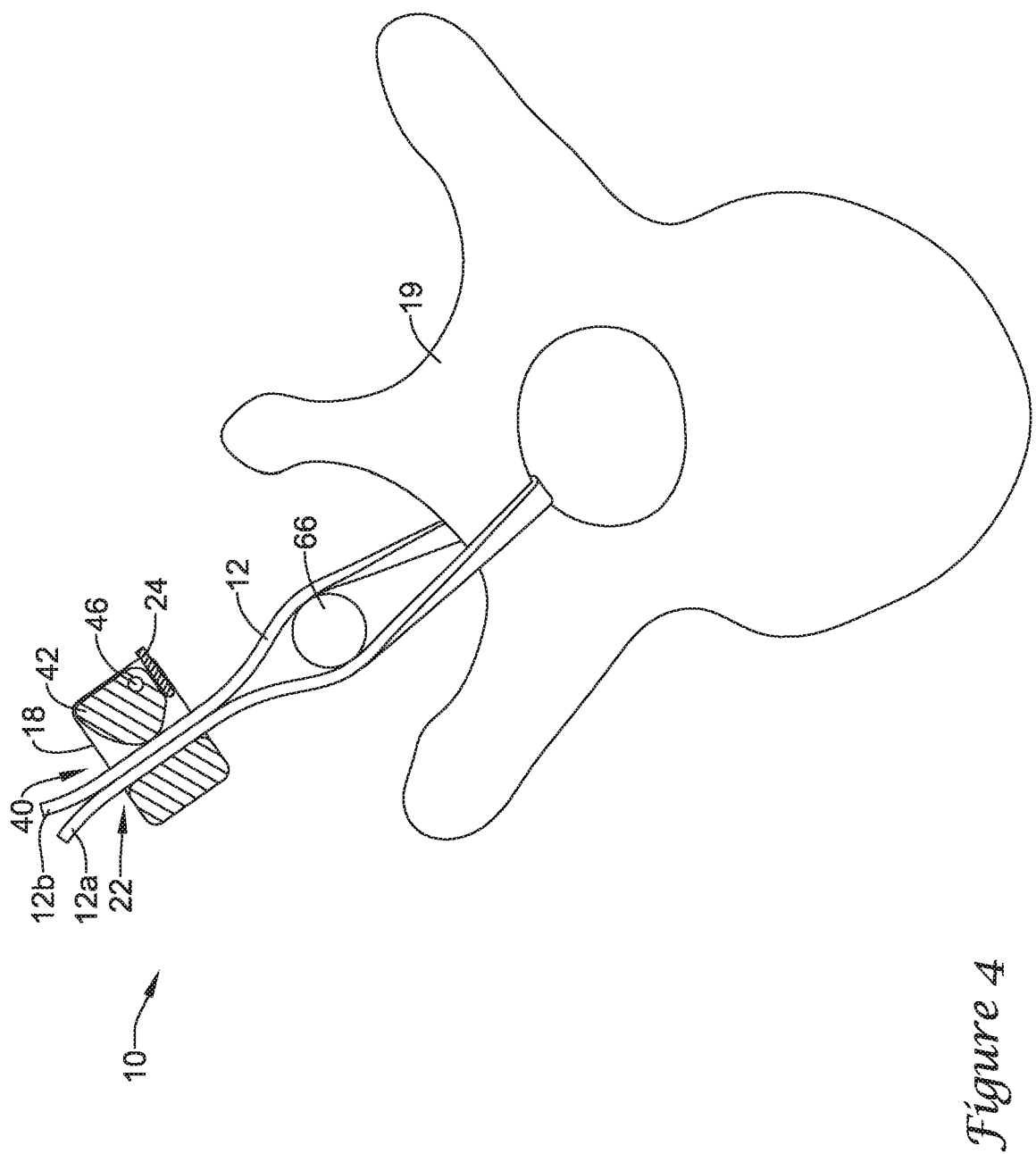
FIG. 4 is a schematic sectional view of a feature of an illustrative vertebral fixing system according to an aspect of the disclosure, where the illustrative vertebral fixing system is engaging a bone structure.

Illustratively, the tightening part 18 may be configured to be in adjustable connection with the flexible elongated member 12. In some cases, the tightening part 18 may include a one-way catch mechanism 22. For example, the one-way catch mechanism may include a pivoted cam-shaped pawl, (as shown in FIG. 4), a zip-tie head, ratcheting teeth, or other fastener features. The one-way catch mechanism 22 may be configured to allow the elongated member 12 to be inserted in a first direction by pulling or moving the elongated member 12 through the tightening part 18 in the first direction. Once the elongated member 12 is inserted, the one-way catch mechanism 22 may be configured to prevent movement of the elongated member 12 through the tightening part 18 in a second direction, substantially opposite the first direction.

In some cases, a cam-shaped pawl portion 40 of the tightening part 18 may include a toothed catch mechanism 42, as shown in FIG. 4, where the catch mechanism 42 may engage the elongated member 12 against a surface of the tightening part 18 to maintain the elongated member 12 in a position with respect to the tightening part 18. The catch mechanism 42 may be spring loaded and/or otherwise biased toward the second direction and may pivot about a pivot feature 46 (e.g., a pin, a screw, a nail, etc.) of the catch mechanism 42. In operation, when the elongated member 12 is moved in the first direction through the cam-shaped pawl 40 of the tightening part 18 or a force in substantially the first direction is applied to the elongated member 12 inserted into the cam-shaped pawl 40 and/or when the release 24 (e.g., a pawl) is pressed against catch mechanism 42, the catch mechanism 42 may pivot about the first pivot feature 46 to allow the elongated member 12 to advance in substantially the first direction. When the elongated member 12 has ceased movement in the first direction and/or the force in substantially the first direction has been removed from the elongated member 12, the catch mechanism 42 may pivot to a resting position such that the catch mechanism 42 engages the elongated member 12 and the side of the tightening part 18 to substantially prevent movement of the elongated member 12 in substantially the second direction.

Figure 5A:
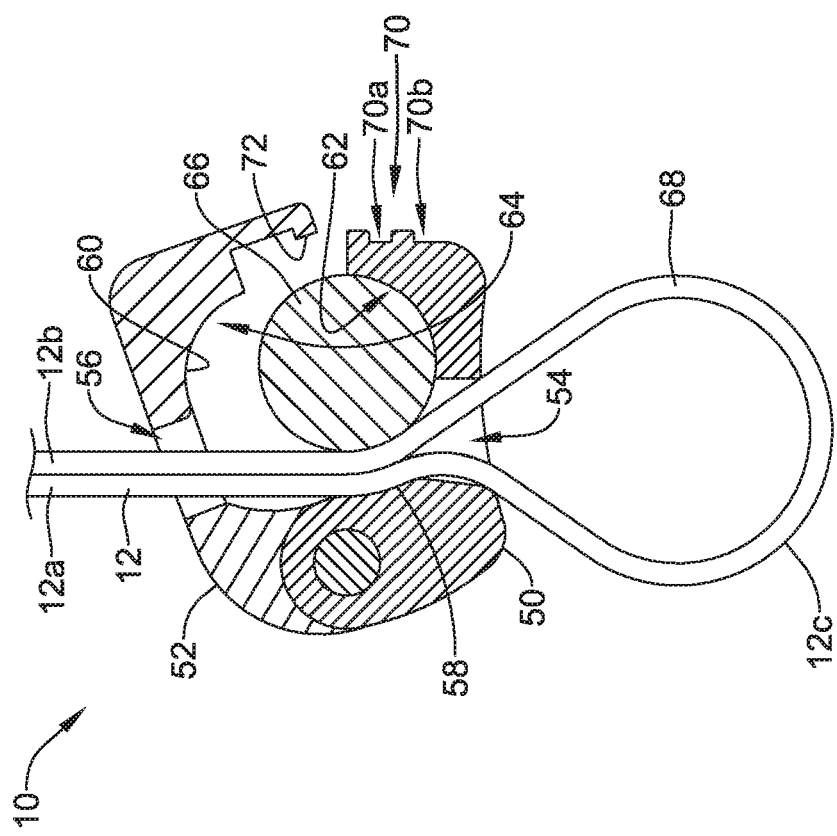
FIG. 5A is a schematic sectional view of an illustrative vertebral fixing system according to an aspect of the disclosure, where the illustrative vertebral fixing system is in an unlocked position.
Figure 5B:
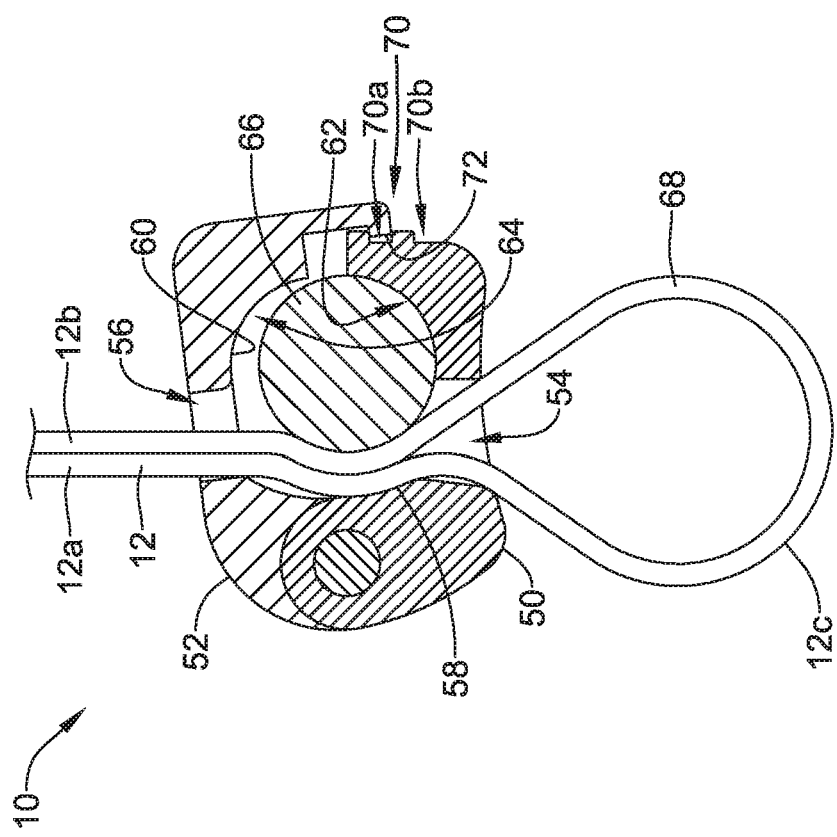
FIG. 5B is a schematic sectional view of the illustrative vertebral fixing system depicted in FIG. 5A, where the illustrative vertebral fixing system is in a preliminary locking position.
Figure 5C:
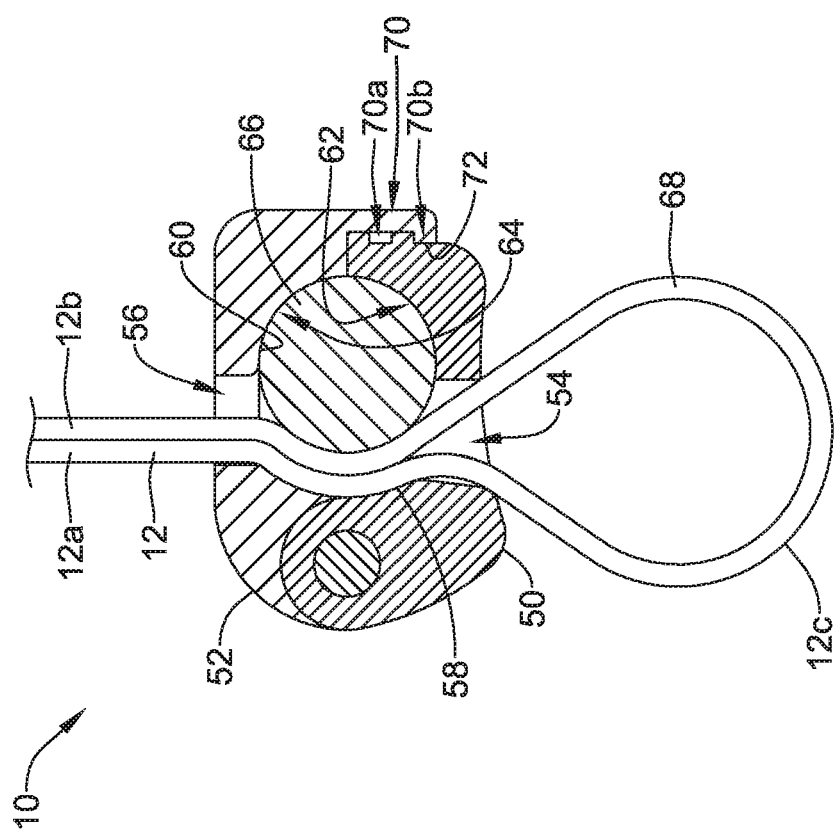
FIG. 5C is a schematic sectional view of the illustrative vertebral fixing system depicted in FIG. 5A, where the illustrative vertebral fixing system is in a final locking position.

Alternatively, or in addition to including a one-way catch mechanism 22, the tightening part 18 or clamping part may have a pivot design, as shown in FIGS. 5A-5C. Illustratively, the tightening part 18 may include a first longitudinal element 50 and a second longitudinal element 52 in a spaced apart position, as shown in FIG. 5A, and configured to pivot about the same axis or different axes. The first longitudinal element 50 and/or the second longitudinal element 52 may be configured to include lock recesses 70. In addition, the first longitudinal element 50 and/or the second longitudinal element 52 may be configured to include a lock tooth or lock teeth 72. The lock teeth 72 on the first longitudinal element 50 and/or the second longitudinal element 52 may be configured to engage the lock recesses(s) 70 of the second longitudinal element 52 and/or the first longitudinal element 50, respectively. For example, as shown in FIGS. 5A-5C, the first longitudinal element 50 may include a first lock recess 70a and a second lock recess 70b and the second longitudinal element 52 may include a lock tooth 72, where the lock tooth 72 may engage the first lock recess 70a when the tightening part 18 is in a preliminary or provisional locking position, as shown in FIG. 5B, and the lock tooth 72 may engage the second lock recess 70b when the tightening part 18 is in a final locking position, as shown in FIG. 5C.

In some cases, the tightening part 18 may take on other configurations and features and/or be combined with other features. Illustrative tightening parts are disclosed in U.S. Pat. Nos. 8,172,843, 7,959,654, and 7,481,828, which are all expressly herein incorporated by reference in their entireties.

In some instances where the tightening part 18 includes a pivot design, the flexible elongated member 12 may be received or engaged in a first opening 54 in the first longitudinal element 50 and a second opening 56 in the second longitudinal element 52 against a portion of a first inside wall 58 of a first recess 62 of the first longitudinal element 50 and/or a second inside wall 60 of a second recess 64 of the second longitudinal element 52. In some cases, a rod 66 may be introduced into the first recess 62 of the first longitudinal element 50 and/or the second recess 64 of the second longitudinal element 52 such that the elongated member 12 may be disposed between the first inside wall 58 and the second inside wall 60 of the first recess 62 and the second recess 64, respectively, and the rod 66.

As shown in FIGS. 5A-5C, the third portion 12c of the elongated member 12 may define a loop 68 that may extend beyond an outer surface of the first longitudinal element 50 or second longitudinal element 52 from the first opening 54. In addition, the first portion 12a of the elongated member 12 and the second portion 12b of the elongated member 12 may extend beyond an outer surface of the second longitudinal element 52 or the first longitudinal element 50 from the second opening 56. When the first longitudinal element 50 and the second longitudinal element 52 are spaced in the provisional locking position, as shown in FIG. 5B, the elongated member 12 may be adjusted for final positioning (e.g., the elongated member 12 may be adjusted and/or tightened for final positioning with the one-way catch mechanism of tightening part 18 described herein, with the first longitudinal element 50, the second longitudinal element 52 and the rod 66, and/or with any other similar or dissimilar tightening mechanism). Provisional positioning of the elongated member 12 may allow for frictional movement of the elongated member within the tightening part 18, for example, to adjust tension in the elongated member 12. Once the third portion 12c of the elongated member 12 forming the loop 68 has been placed around a bone (e.g., a vertebra, rib, or other bone structure 19) or other object and the elongated member is in its final position, a user (e.g., a surgeon) may further engage the second longitudinal element 52 with the first longitudinal element 50 to place the tightening part 18 in the final locking position. Final locking of the elongated member 12 within the tightening part 18 may fix the elongated member 12 in relation to the tightening part 18 or clamping member preventing further movement of the elongate member 12 through the tightening part 18. This multi-step locking system of the tightening part 18 may allow the user to extract traction on the elongated member 12 around the bone or other object and once the tension in the elongated member 12 is sufficient for providing appropriate fastening, the user may finish the tightening process by applying a force to the second longitudinal element 52 to move the second longitudinal element 52 to the final locking position with respect to the first longitudinal element 50.

Figure 6:
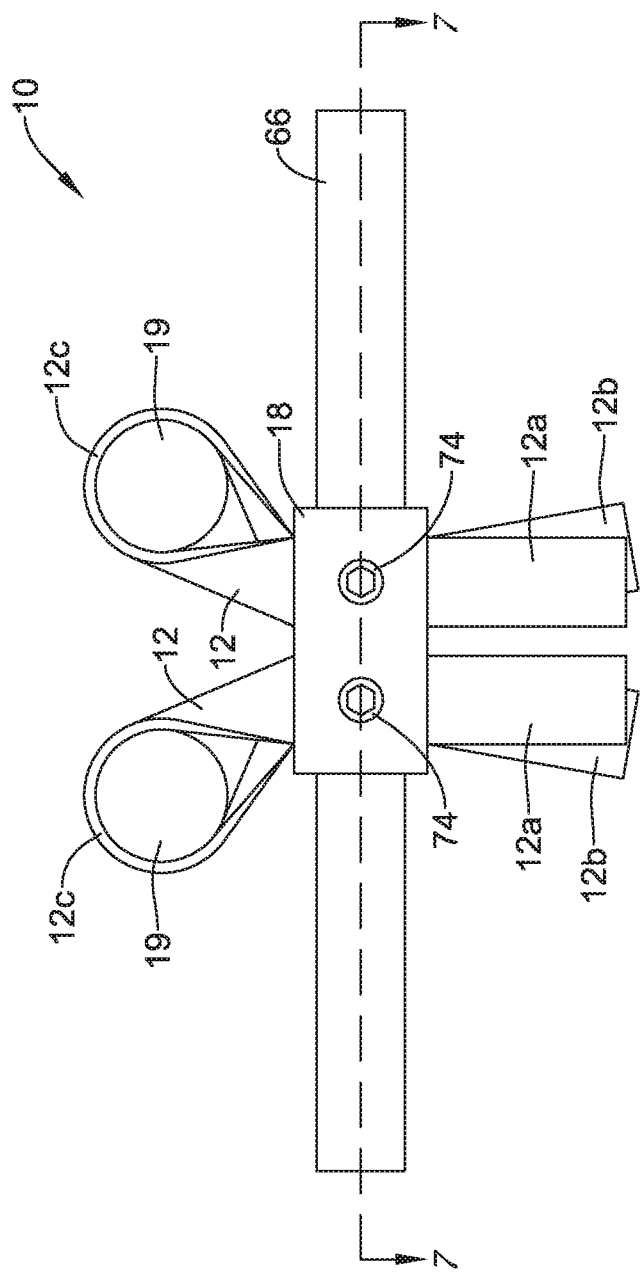
FIG. 6 is a schematic plan view of an illustrative vertebral fixing system according to an aspect of the disclosure, where the illustrative vertebral fixing system is engaging a bone structure.
Figure 7:
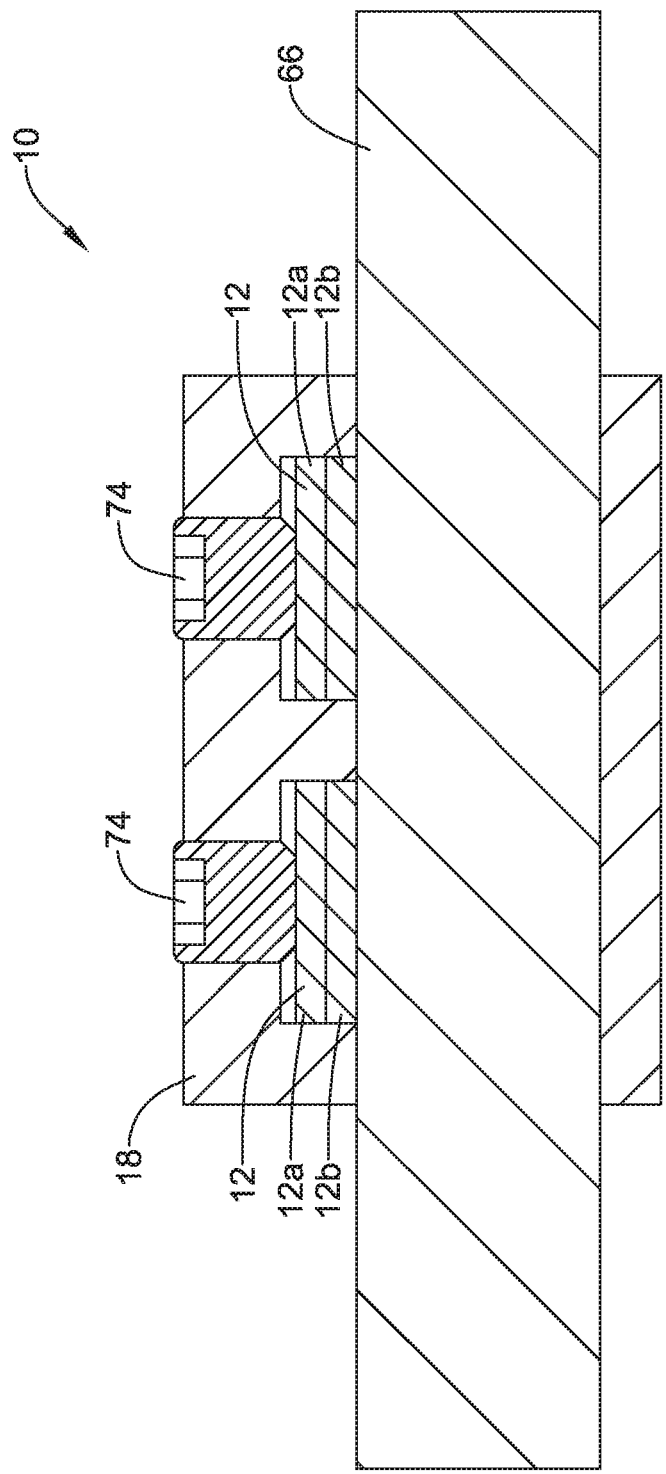
FIG. 7 is a schematic sectional view of the illustrative vertebral fixing system of FIG. 6.

In some instances, the tightening part 18 may be configured to receive and/or engage a plurality of elongated members 12. For example, as shown in FIGS. 6 and 7, the tightening part 18 may be configured to receive and/or engage two elongated members 12. Illustratively, the tightening part 18 receiving a plurality of elongated members 12 may be configured to tighten each elongated member 12 separately from the others or tighten each elongated member 12 at the same time, where the tightening of the elongated members 12 may be performed with a one-way catch mechanism 22, a set screw 74 and a pressure fit, and/or with any other similar or dissimilar device. Further, the tightening part 18 receiving the plurality of elongated members 12 may be configured to lock each of the plurality of elongated members 12 independently of one another or substantially simultaneously, where the elongated members 12 may be locked in place using teeth and teeth recesses to provisionally lock and finally lock the elongated members 12 in place, using a tightening set screw 74 for each elongated member 12, as shown in FIGS. 6 and 7, a single tightening set screw 74 for the elongated members 12, and/or any other locking or tightening features, as desired.

Figure 14:
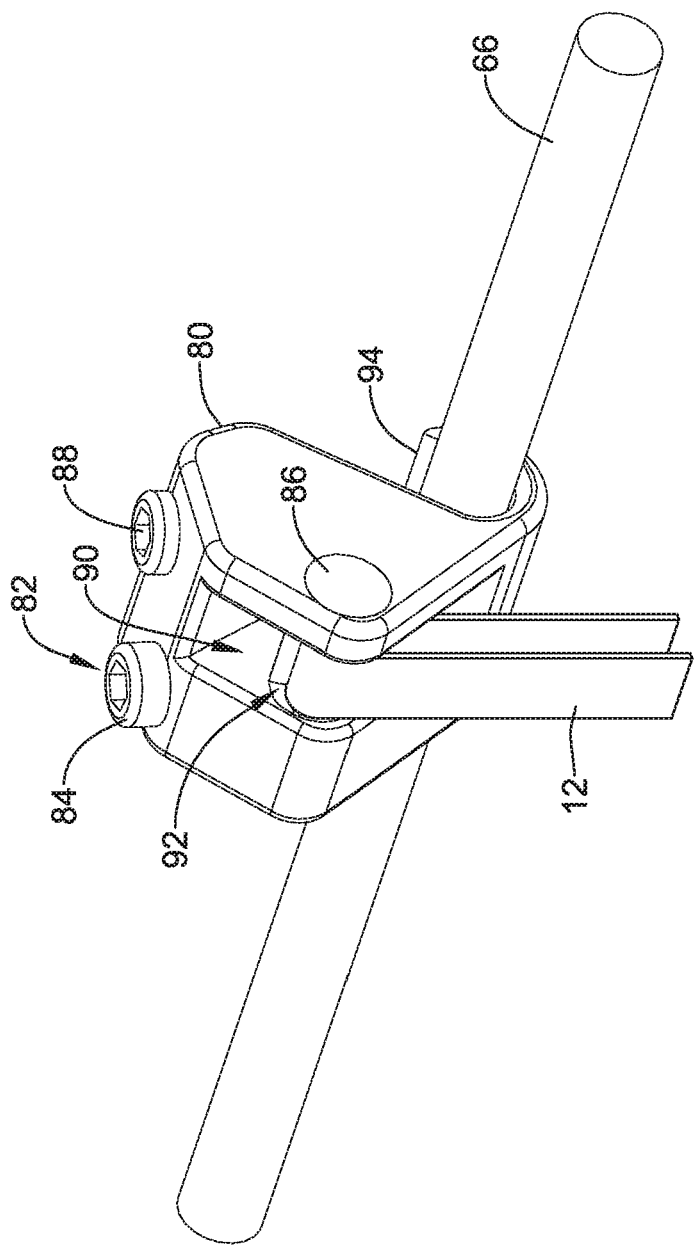
FIG. 14 is a schematic perspective view of an illustrative vertebral fixing system according to an aspect of the disclosure.
Figure 15:
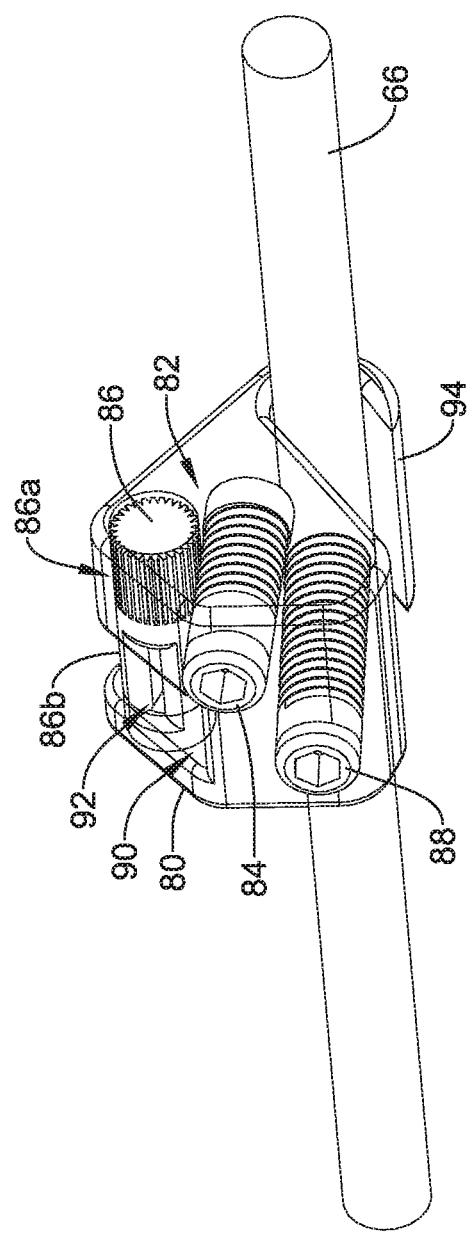
FIG. 15 is a schematic perspective view of illustrative interior features of the illustrative vertebral fixing system depicted in FIG. 14, where a housing of the illustrative vertebral fixing system is depicted as being transparent.

In some instances, the tightening part 18 may be configured to allow for post-operative and/or percutaneous adjustability of tension in the elongated member 12 received and/or engaged by the tightening part 18 and/or of the positioning of the tightening part 18 with respect to the rod 66. Illustratively, such a tightening part 18, as shown in FIGS. 14 and 15, may include a housing 80, a worm drive 82 having a screw 84 and a worm gear 86, a rod locking screw 88, and/or other features, as desired. As shown in FIG. 14, the housing 80 may have an opening 90, where the worm gear 86 of the worm drive 82 may extend substantially across the opening 90. The opening 90 may be any shape and/or size configured to receive the elongated member 12. In some instances, the housing 80 may include a cover at least partially enclosing the opening 90, where the cover may have a slit(s) or slot(s) for receiving the elongated member 12. Further, the screw 84 of the worm drive 82 and the rod locking screw 88 may be configured to extend from the same side of the housing 80, such that a user (e.g., a surgeon) may access the screw 84 of the worm drive 82 and the rod locking screw 88 at a substantially same angle or access point with respect to the housing 80.

The worm gear 86 may have a geared portion 86a and a receiving portion 86b, where the geared portion 86a may be configured to engage the screw 84 and the receiving portion 86b may be configured to receive the elongated member(s) 12. The receiving portion 86b may include a slot 92 through which the elongated member(s) 12 may be received, engaged, and/or wrapped. In some cases, the slot 92 of the receiving portion 86b of the worm gear 86 may clamp the received elongated member(s) 12 and/or the receiving portion 86b of the worm gear 86 may otherwise engage the elongated member(s) 12 to facilitate adjusting a tension in the elongated member 12 when the worm gear 86 is rotated. Alternatively, or in addition, the elongated member 12 may be mechanically attached to the receiving portion 86b of the worm gear 86 and/or the elongated member 12 may be wrapped around worm drive 82.

In operation, once the elongated member(s) 12 have been received by the receiving portion 86b of the worm gear 86, the screw 84 of the worm drive 82 may be adjusted to adjust a tension in the received elongated member(s) 12. To adjust the tension in the received elongated member(s) 12, the screw 84 of the worm drive 82 may be rotated, such as with an elongated driver, which causes the worm gear 86 to rotate and adjust the tension in the received elongated member(s) 12.

Figure 16:
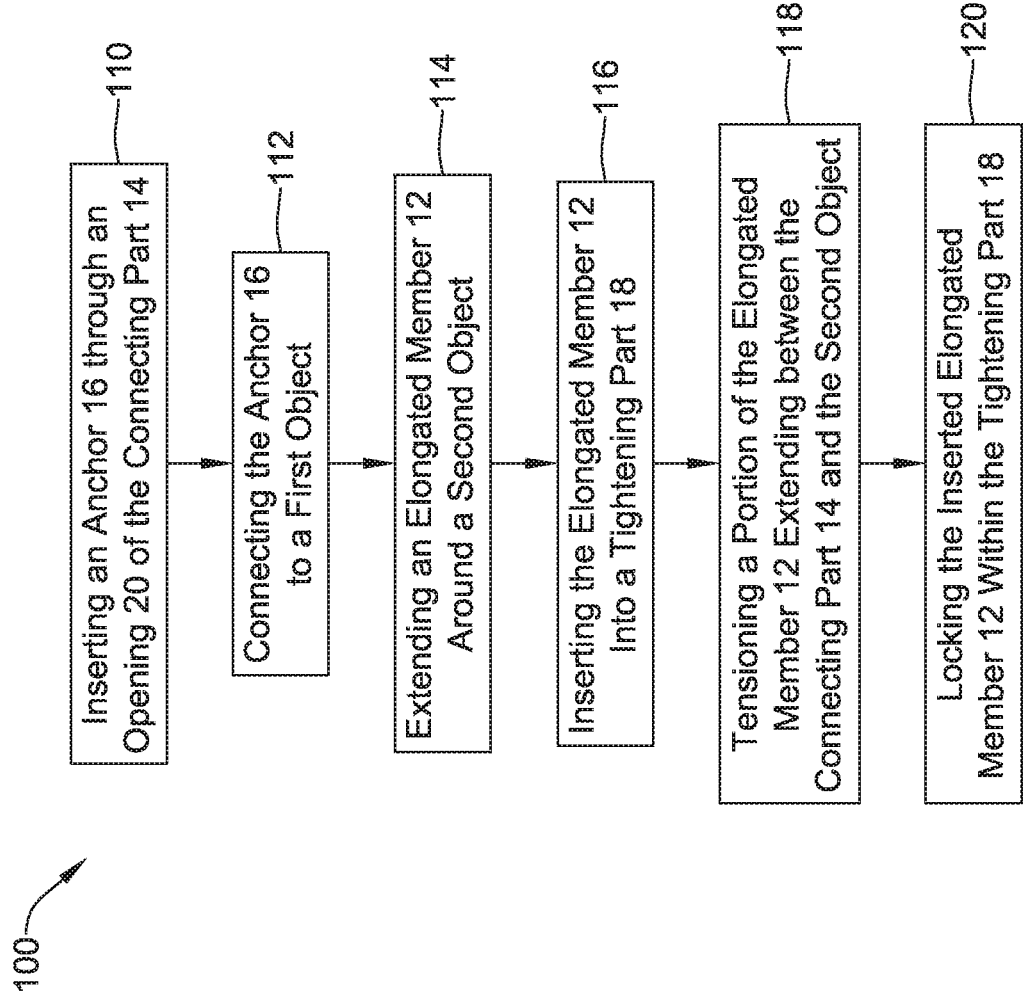
FIG. 16 is a schematic flow diagram of an illustrative method for manipulating spinal anatomy using an illustrative vertebral fixing system according to an aspect of the disclosure.

The housing of the tightening part 18 may include an opening (e.g., a hook, U-shaped channel, through hole, or other opening) 94 configured to engage and/or receive the rod 66, as shown in FIGS. 15 and 16. To facilitate securing the housing 80 to the rod 66, the rod locking screw 88 may be adjusted (e.g., rotated) such that it engages the rod 66 received in the opening 94. The tightening of the rod locking screw 88 may apply a force to the rod 66 to secure the housing 80 at a position with respect to the rod 66. Alternatively, or in addition, the rod locking screw 88 may be configured to facilitate securing the housing 80 at a position with respect to the rod 66 through any connection technique including, but not limited to, engaging an opening in the rod 66, and/or any other similar or dissimilar connection technique, as desired.

In such an embodiment, during a medical procedure the tightening part 18 may be inserted through an incision of the patient and be secured to a rod 66 or other construct installed on the vertebrae. Then the elongated member 12 may be tightened to a desired amount by rotating the worm gear 86 via the worm drive 82 with a driver instrument during the medical procedure. Thereafter, the incision may be closed at the conclusion of the medical procedure. In a subsequent revision medical procedure, a small access incision may be made in the patient to gain access to the previously installed tightening part 18, and a driver instrument may be minimally invasively or percutaneously inserted through the small access incision to further adjust the tension of the elongate member 12. For example, the driver instrument may be used to rotate the worm gear 86 via the worm drive 82 in order to adjust the amount of tension applied to the elongate member 12 (e.g., apply less tension or apply more tension). The access incision need only be large enough to advance the elongate shaft of the driver instrument to the driver interface of the worm drive 82, and thus the access incision may not be large enough to pass the tightening part 18 therethrough.

In some instances, the vertebral fixing system 10 may include a spacer 26 (e.g., a bumper). The spacer 26 may be made of any material. For example, the spacer 26 may be made of a metal material, a polymer material, or any other similar or dissimilar material, as desired. In some cases, the spacer 26 may be rigid or inflexible, while in other instances the spacer 26 may be flexible or elastically yielding.

Figure 8:
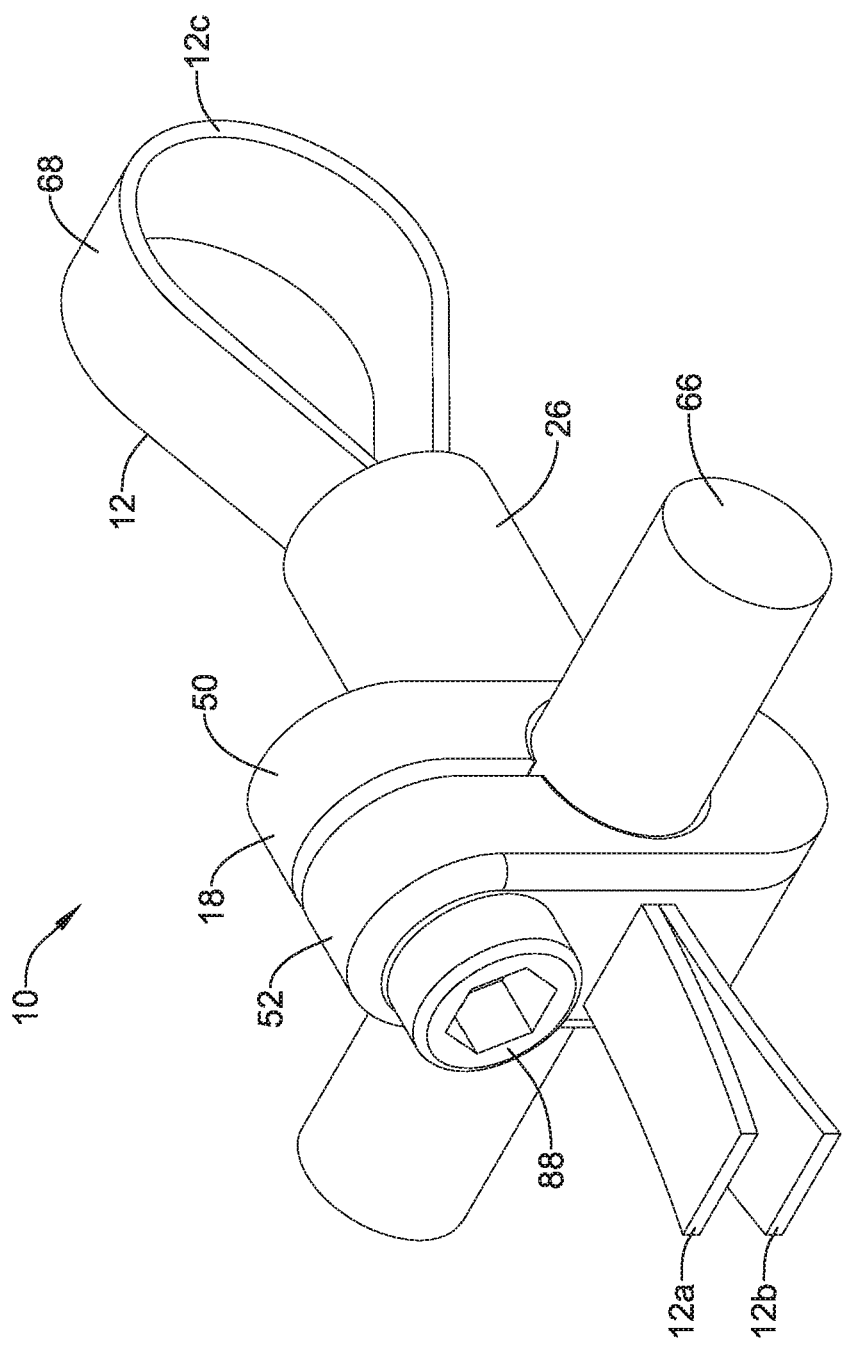
FIG. 8 is a schematic perspective view of an illustrative vertebral fixing system including a spacer according to an aspect of the disclosure.

An illustrative spacer 26 may have a first opening 28a at or near a first end of the spacer 26, a second opening 28b at or near a second end of the spacer 26, and an extending portion 30 extending between the first end at or near the first opening 28a of the spacer 26 and the second end at or near the second opening 28b of the spacer 26. Illustratively, the spacer 26 may be configured to extend between the bone structure 19 and a tightening part 18 (as shown in FIG. 8, where loop 68 may be configured to be wrapped around a bone structure 19), two bone structures 19 (as shown in FIGS. 9 and 10), and/or between other similar or dissimilar features, as desired.

Figure 9:
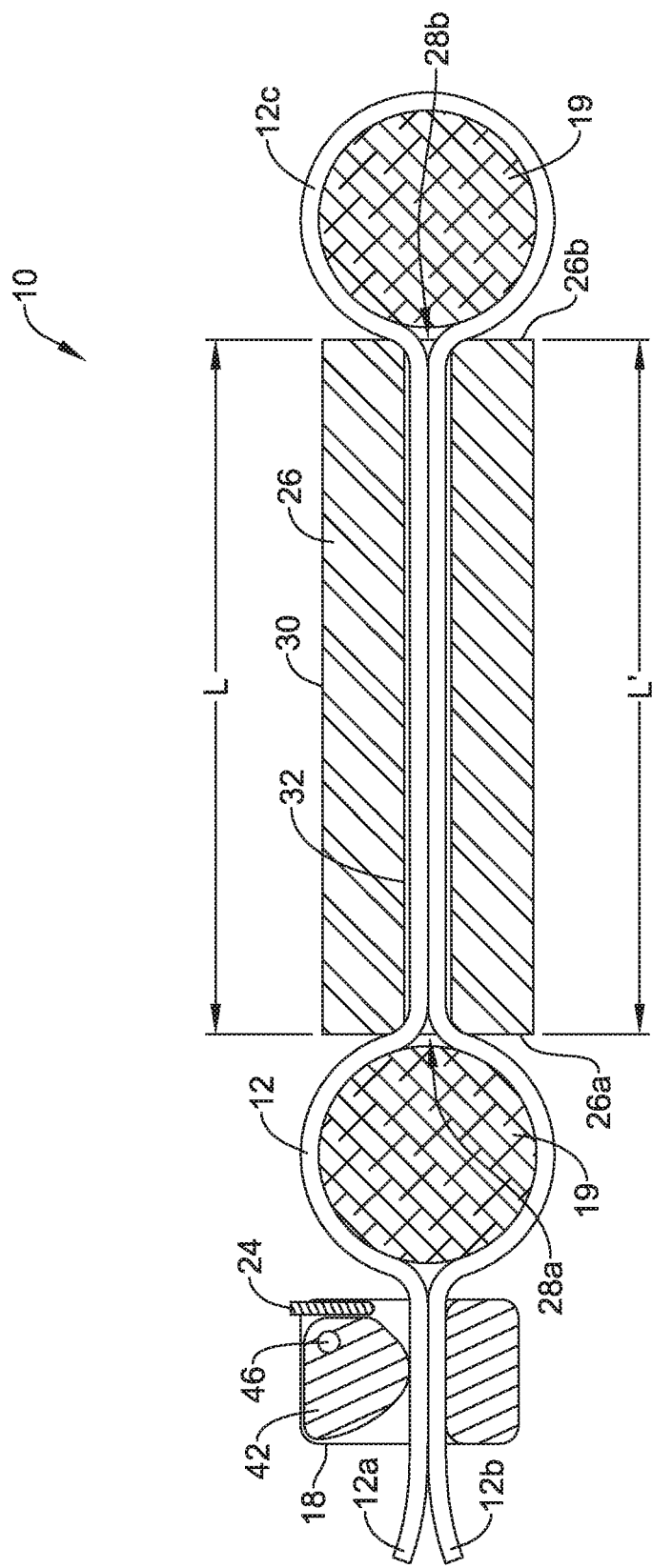
FIG. 9 is a schematic sectional view of an illustrative vertebral fixing system including a spacer according to an aspect of the disclosure, where the illustrative vertebral fixing system is engaging a bone structure.
Figure 13:
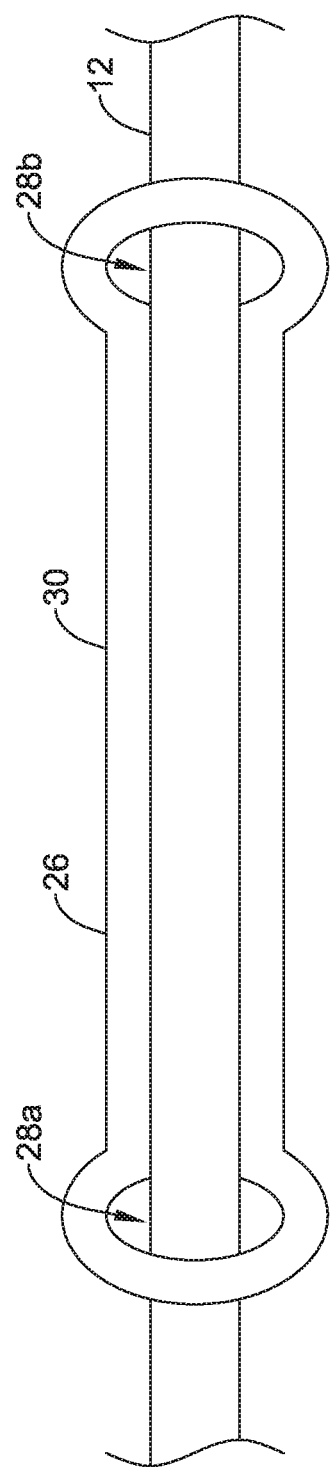
FIG. 13 is a schematic side view of an illustrative vertebral fixing system including an elongated member and a spacer according to an aspect of the disclosure.

In some cases, the extending portion 30 of the spacer 26 may at least partially define a lumen 32, as shown in FIG. 9. Alternatively, or in addition, the extending portion 30 may be substantially flat or collapsible such that the elongated member 12 may pass through the first opening 28*a* of the spacer 26, travel along the extending portion 30, and pass through the second opening 28*b* of the spacer 26, as shown in FIG. 13.

The spacer 26 may have a length L extending substantially from the first end of the spacer 26 to the second end of the spacer 26 and the lumen 32 may have a length L' substantially equal to the length L of the spacer 26, as shown in FIG. 9, or any other length dimension, as desired. Illustratively, the spacer 26 may receive the elongated member 12 in the first opening 28*a* of the spacer 26 and/or in the second opening 28*b* of the spacer 26, wherein the received elongated member 12 may extend along the spacer 26 and/or at least partially extend through the lumen 32. In use, the spacer 26 may be held in compression while the elongated member 12 may be held in tension.

Figure 10:
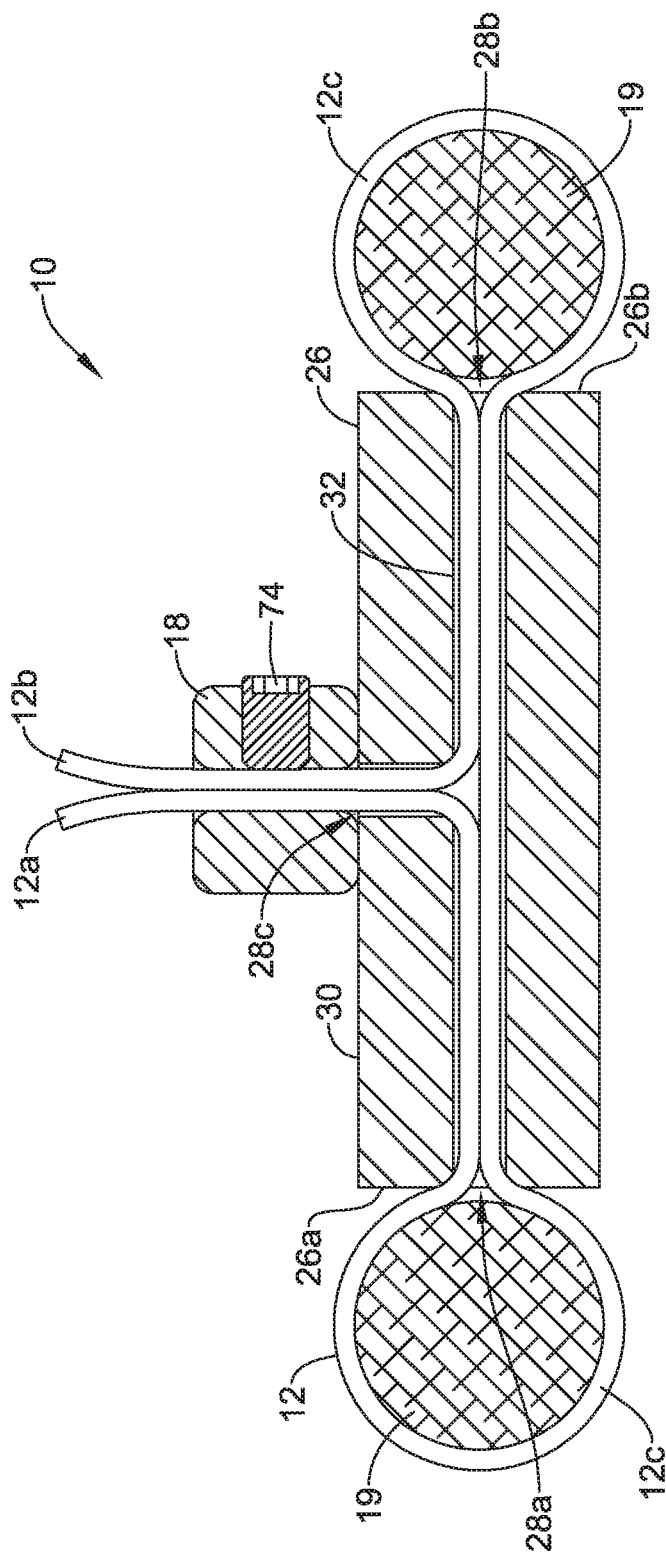
FIG. 10 is a schematic sectional view of an illustrative vertebral fixing system including a spacer according to an aspect of the disclosure, where the illustrative vertebral fixing system is engaging a bone structure.

As shown in FIG. 10, the spacer 26, in some cases, may include a third opening 28*c* (e.g., an intermediate opening of the spacer 26). The third opening 28*c* may be positioned, for example, at a location between the first opening 28*a* of the spacer 26 and the second opening 28*b* of the spacer 26. Alternatively, or in addition, the third opening 28*c* may be an intermediate opening positioned between a first end 26*a* and a second end 26*b* of the spacer 26. In some illustrative cases, where the spacer 26 may include the lumen 32, the third opening 28*c* may communicate with the lumen 32.

Illustratively, the spacer 26 may receive the elongated member 12 through the first opening 28*a* of the spacer 26 and/or the second opening 28*b* of the spacer 26, where the elongated member 12 may extend along at least a portion of the spacer 26. For example, the elongated member 12 (e.g., a first portion 12*a*, or other portion, of the elongated member 12) may extend into the first opening 28*a* of the spacer 26 and/or the elongated member 12 (e.g., a second portion 12*b*, or other portion, of the elongated member 12) may extend into the second opening 28*b* of the spacer 26 and at least a part of the elongated member 12 (e.g., the first portion 12*a*, the second portion 12*b*, and/or the third portion 12*c*, or other portion of the elongated member 12) inserted into and/or through the first opening 28*a* of the spacer 26 and/or the second opening 28*b* of the spacer 26 may extend through the third opening 28*c* of the spacer 26, as shown in FIG. 10. In the example, the portion(s) of the elongated member 12 inserted into and/or through the third opening 28*c* may be received and/or engaged by the tightening part 18. In some instances, the tightening part 18 may engage the elongated member 12 at a position adjacent the third opening 28*c*.

Figure 11:
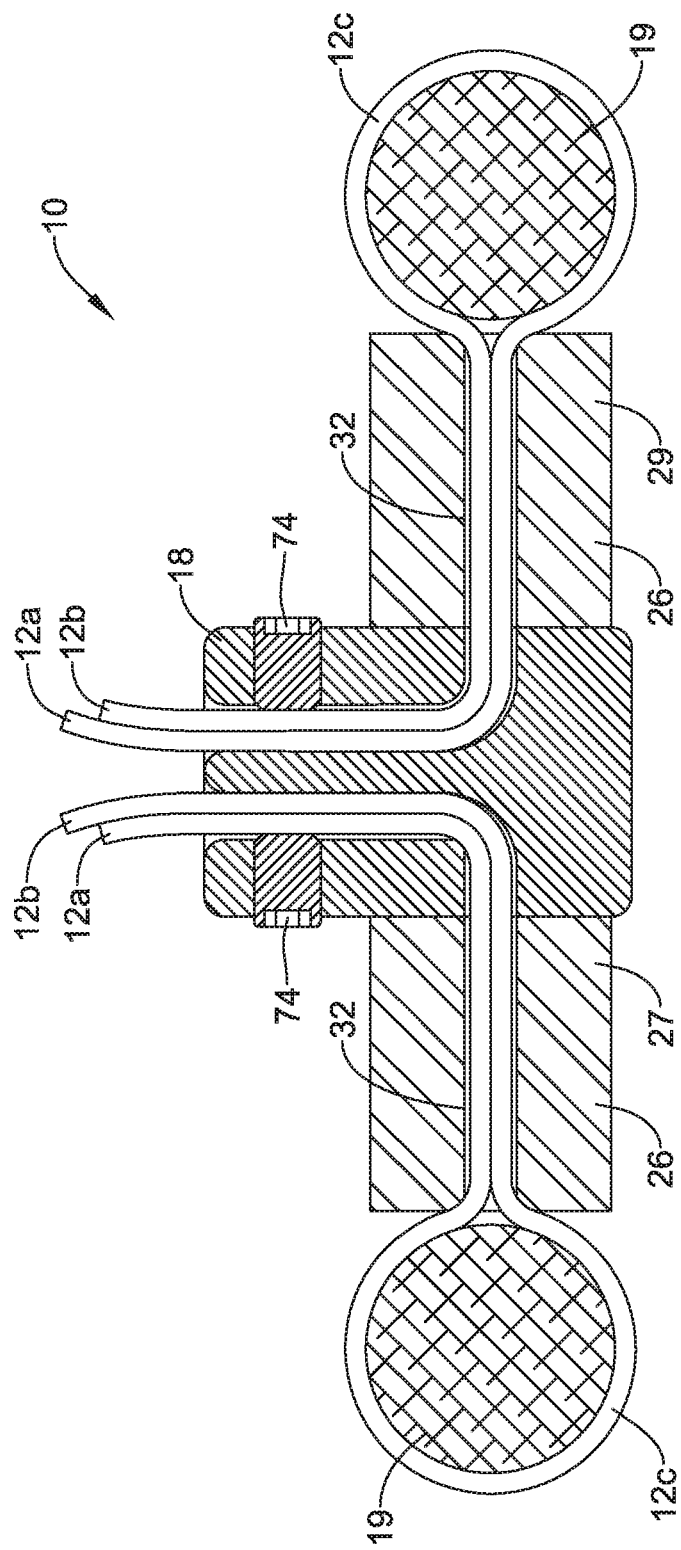
FIG. 11 is a schematic sectional view of an illustrative vertebral fixing system including a spacer according to an aspect of the disclosure, where the illustrative vertebral fixing system is engaging a bone structure.

In FIG. 11, an illustrative vertebral fixing system 10 is depicted that may include two elongated members 12, a tightening part 18, and two spacers 26 (e.g., a first spacer 27 and a second spacer 29). In some instances, a first elongated member 12 may be wrapped around a bone structure 19, inserted through the first spacer 27, and inserted into the tightening part 18 to apply and/or maintain a tension in the first elongated member 12 and maintain the first spacer 27 in a position with respect to the bone structure 19. Similarly, a second elongated member 12 may be wrapped around a bone structure 19, inserted through the second spacer 29, and inserted into the tightening part 18 to apply and/or maintain a tension in the second elongated member 12 and maintain the second spacer 29 in a position with respect to the bone structure 19. In some cases, the tightening part 18 may abut the first spacer 27 and/or the second spacer 29, as shown in FIG. 11. Alternatively, or in addition, the tightening part 18 may receive and/or engage the first spacer 27 and/or the second spacer 29.

As an alternative to the tightening part 18 having separate pathways for each elongated member 12, as shown in FIG. 11, the tightening part 18 may have a single pathway or interconnected pathways configured to receive a single elongated member or multiple elongated members. For example, a single elongated member 12 may be used with two spacers and one tightening member, where the single elongated member 12 may be wrapped around two bone structures 19, rods 66, other structures, or combinations thereof, and passed through a single pathway or interconnected pathways of the tightening part 18 (e.g., two discrete juxtaposed portions of 12 may pass through a single pathway of the tightening part 18).

As shown in FIGS. 10 and 11, set screws 74 of tightening part 18 may engage the elongated members 12. The set screws 74 may be configured to engage and tighten the elongated member(s) 12 inserted through the spacer 26 and/or tightening part 18. For example, the set screw(s) 74 may be configured to engage the elongated member(s) 12 and tighten the elongated member(s) 12 in a manner that holds the elongated member(s) 12 in a position relative to the tightening part 18.

Figure 12A:
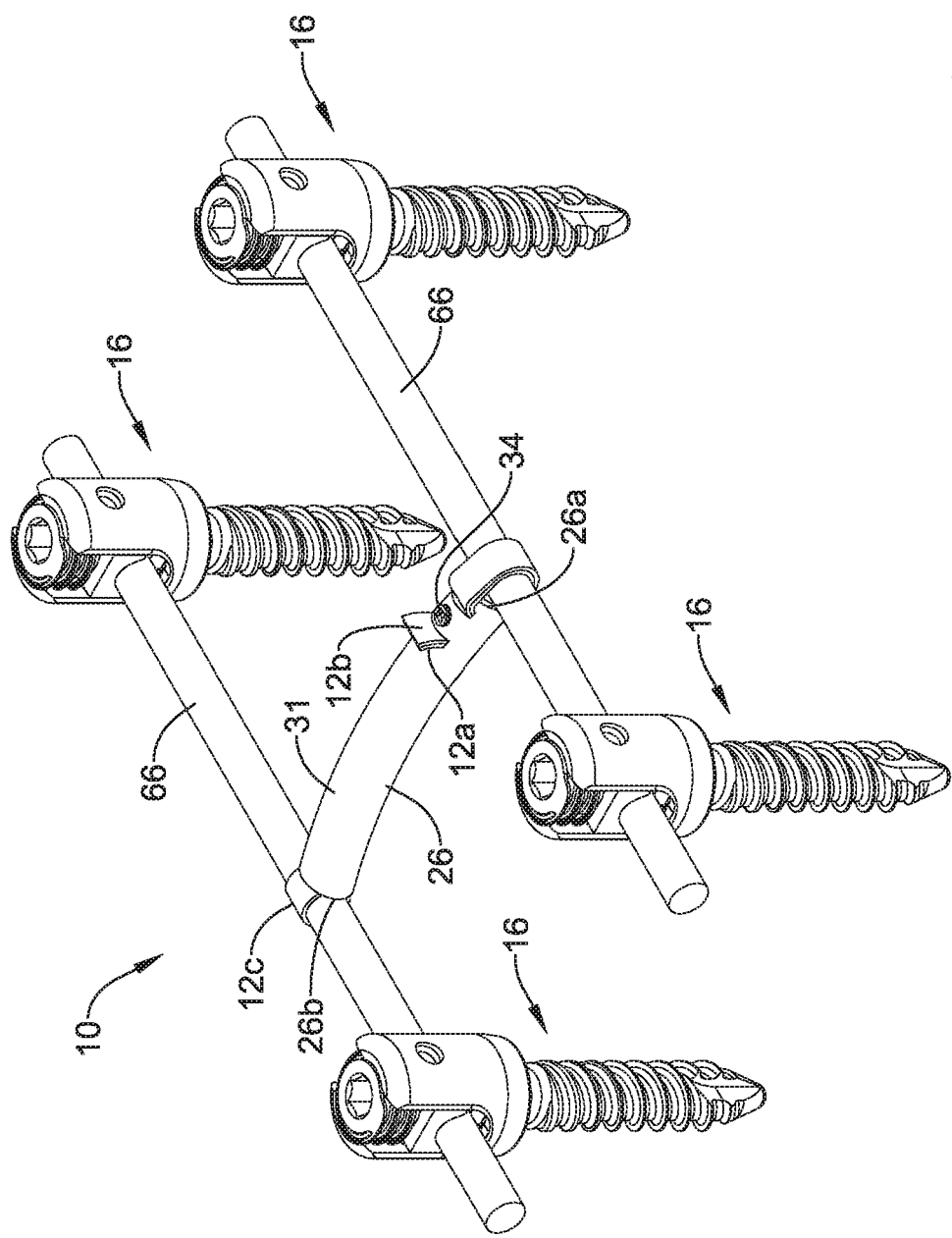
FIG. 12A is a schematic perspective view of an illustrative vertebral fixing system including an elongated member and a spacer according to an aspect of the disclosure.
Figure 12B:
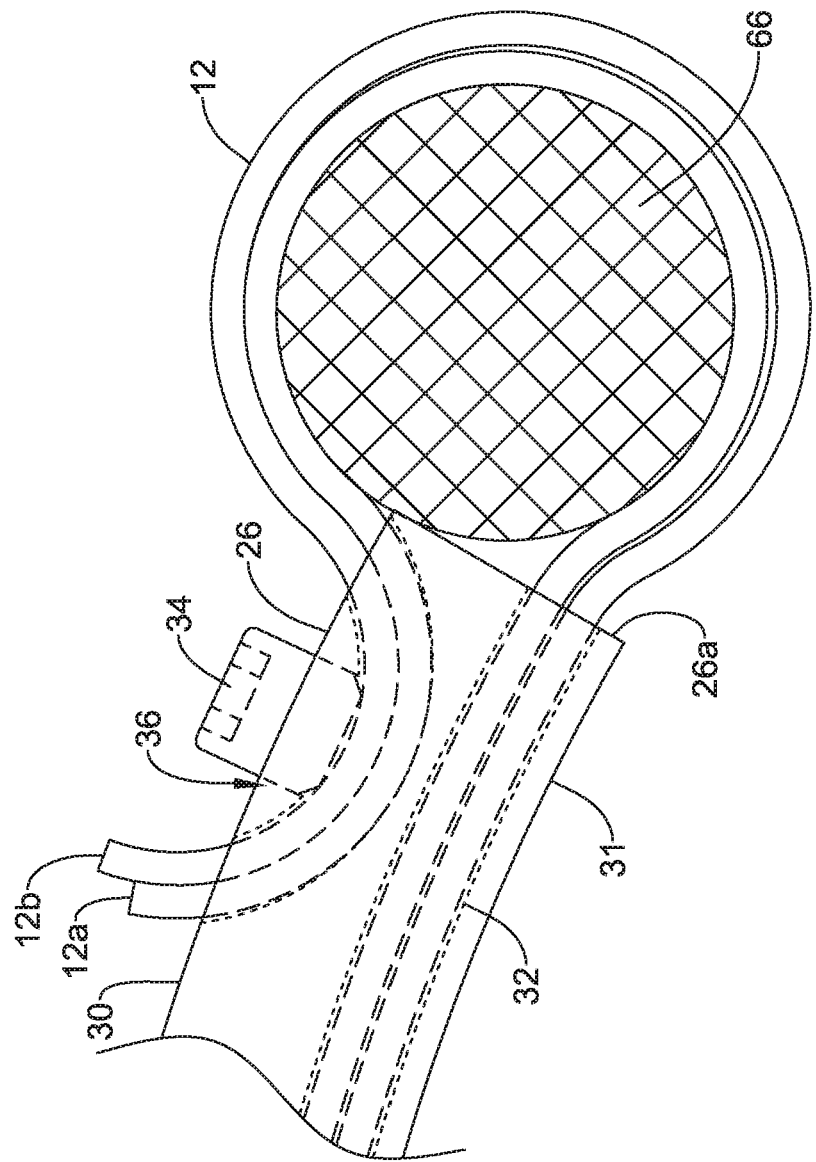
FIG. 12B is an expanded schematic side view taken of the illustrative vertebral fixing system including a spacer depicted in FIG. 12A, where the dotted lines show features interior of the spacer.

In some illustrative instances, set screw(s) 34 may engage the spacer 26 (e.g., a bumper and/or a cross-link connector), as shown in FIGS. 12A and 12B. The set screw(s) 34 may be configured to engage any portion of the spacer 26 (e.g., at or near the first end 26*a* of the spacer 26, the second end 26*b* of the spacer 26, and/or another portion of the spacer 26). The set screw(s) 34 may be configured to extend through a set screw opening 36 extending partially through the spacer 26 or all of the way through the spacer 26. The set screw(s) 34 may engage a hole or opening in the elongated member 12 (e.g., through which a portion of the elongated member 12 may extend) and/or may trap the elongated member 12 between the set screw(s) 34 and a surface the spacer 26, such that the set screw 34 may act on the elongated member 12 to maintain the engaged portion of the elongated member 12 in a desired position relative to the set screw 34.

In some cases, the set screw 34 may engage a portion of the elongated member 12 within the lumen 32 of the spacer 26 and/or may engage a portion of the elongated member 12 extending exterior the spacer 26. For example, the elongated member 12 may be extended through the lumen 32 of the spacer 26, around a bone or rod, optionally through another spacer 26, and back to the spacer 26 with the set screw(s) 34, where the set screw 34 may engage the extended and wrapped elongated member 12 to secure the spacer 26 adjacent or to the bone or rod, as desired. The spacer 26 including the set screw(s) 34 may be used for other purposes and with other techniques where the set screw(s) 34 may be configured to engage the elongated member 12. In some cases, the spacer 26 with the set screw(s) 34 may be utilized as an intermediate component between the elongated member 12 and the bone structure 19.

As shown in FIGS. 12A and 12B, the spacer 26 and the elongated member 12 may be a cross-link connector 31 or transverse connector extending between two rods 66. Alternatively or in addition, the cross-link connector 31 may extend between rods 66, bone structures, anchors, and/or a combination thereof. Illustratively, one of the rods 66 may be configured to extend along a spinal column on a first side of the spinal process and a second rod 66 may be configured to extend along the spinal column on a second side of the spinal process, where the rods 66 may be secured with respect to the spinal column via anchors 16 (e.g., mono-axial pedicle screws, poly-axial pedicle screws, bone anchors, or other securing mechanisms). In some instances, the rods 66 may be located a distance apart and the cross-link connector 31 may be configured to extend substantially the distance between the two rods 66 and receive the elongated member 12. For example, the elongated member 12 may be configured to be wrapped around one of the rods 66 or otherwise secured to the rod 66, extended through at least a portion of the cross-link connector 31, wrapped around another of the rods 66 or otherwise secured to the another of the rods 66, and tightened and/or secured with respect to the cross-link connector 31 through tightening of the set screw(s) 34. Such an arrangement of the cross-link connector 31 may add stability to the positioning of the rods 66 with respect to one another and/or have other benefits.

Illustratively, the vertebral fixing system 10 may used in a method 100 for manipulating spinal anatomy. For example, the anchor 16 may be inserted through an opening 20 of the connecting part 14 (step 110), such that the elongated member 12 may be connected to the connecting part 14. In some cases, the anchor 16 may engage or connect to the connecting part 14 in any other manner, as desired. After or before (or while) the elongated member 12 is (being) inserted through the opening 20 of the connecting part 14, the anchor 16 may be connected (e.g., through a screwing technique or other connecting technique facilitated by the design and/or structure of the anchor 16) to a first object (e.g., first portion of the spinal anatomy, a rod 66, etc.) (step 112) to secure the connecting part 14 relative to the first object. The elongated member 12 connected to the connecting part 14 may be extended around (or otherwise put in communication with) a second object (e.g., a second portion of the spinal anatomy, a rod 66, etc.) (step 114). Further, a first portion 12*a* and/or a second portion 12*b* of the elongated member 12 may be inserted into or otherwise engage a tightening part 18 (step 116). For example, once the elongated member 12 has been extended around the second object, the first portion 12*a* and/or the second portion 12*b* of the elongated member 12 may be inserted into the tightening part 18. A user may tension a portion of the elongated member 12 extending between the connecting part 14 and the second object with the tightening part 18 or any other feature (step 118). The tension may be applied in any manner. For example, the tensioning (step 118) may be applied by pulling the elongated member 12 around the spinal anatomy and through the tightening member 18 with a tensioning device and/or in any other manner, as desired. Once a desired tension has been applied to the elongated member 12, the elongated member 12 inserted into the tightening part 18 may be locked or fixed (step 120) within the tightening part 18 to maintain a tension in the tensioned portion of the elongated member 12.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A vertebral fixing system, comprising:
a flexible elongated member having a first portion, a second portion, and an intermediate portion extending between the first portion and the second portion;
a spacer, wherein the flexible elongated member passes through the spacer;
a tightening part engaging the flexible elongated member, wherein the tightening part is configured to secure the flexible elongated member with respect to the spacer; and
wherein one or both of the first portion of the flexible elongated member and the second portion of the flexible elongated member are configured to be wrapped around a bone and inserted into the tightening part, the tightening part configured to cinch the bone toward the tightening part using the flexible elongated member while the spacer maintains a distance between the bone and the tightening part by engaging the tightening part;
wherein the tightening part uses the flexible elongated member to tighten the spacer and tightening part against each other along the flexible elongated member such that the bone, spacer and tightening part are configured to be aligned in a row extending along a medial-lateral axis.

2. The system of claim 1, further comprising:
a connecting part; and
a bone anchor configured to be inserted through an opening of the connecting part and to engage a bone.

3. The system of claim 1, wherein the tightening part engages the first portion of the flexible elongated member and the second portion of the flexible elongated member to secure a loop formed by the intermediate portion of the flexible elongated member with respect to the spacer.

4. The system of claim 1, wherein the tightening part includes:
a one-way catch mechanism; and
a release to allow for adjustment of the flexible elongated member with respect to the bone.

5. The system of claim 1, wherein the spacer comprises:
a first opening, a second opening, and an extending portion extending between the first opening of the spacer and the second opening of the spacer; and
wherein the spacer receives the flexible elongated member in the first opening of the spacer and the second opening of the spacer.

6. The system of claim 5, wherein:
the spacer has a lumen; and
the spacer receives the flexible elongated member in the lumen.

7. The system of claim 6, wherein:
the spacer has a length extending from the first opening of the spacer to the second opening of the spacer;
the lumen has a length equal to the length of the spacer; and
the flexible elongated member extends into a first end of the lumen, along the length of the lumen, and out of a second end of the lumen.

8. The system of claim 6, wherein: the tightening part has a first passage extending into the tightening part and a second passage intersecting the first passage at an angle.

9. The system of claim 5, further comprising:
a set screw engaging the tightening part; and
the set screw engaging at least one of the first portion of the flexible elongated member, the second portion of the flexible elongated member and the intermediate portion of the flexible elongated member.

10. The system of claim 1, wherein the flexible elongated member is configured to be drawn in a direction perpendicular to an axis along which the bone, spacer and tightening part are configured to align.

11. The system of claim 1, further comprising an additional spacer, wherein:

the spacer and the additional spacer are disposed on opposite sides of the tightening part;

the flexible elongated member extends through the spacer and the additional spacer; and the tightening part is configured to draw the bone and an additional bone or rod toward each other and a center of the vertebral fixing system using the flexible elongated member.

12. A vertebral fixing system, comprising:
a flexible elongated member having a first portion, a second portion, and an intermediate portion extending between the first portion and the second portion;
a spacer comprising:
an extender portion extending between a first end and a second end; and
a lumen extending through the extender portion to form a first outlet and a second outlet;
wherein the first portion and the second portion of the flexible elongated member extend from the lumen at the first outlet, and the intermediate portion of the flexible elongated member extends from the lumen at the second outlet to form a loop;
a tightening part engaging the flexible elongated member, wherein the tightening part is configured to secure the flexible elongated member with respect to the spacer;
an additional spacer having an additional lumen extending therethrough; and
an additional flexible elongated member extending through the additional lumen;
wherein the tightening part includes an additional passage for receiving the additional flexible elongated member.

13. The system of claim 12, further comprising a rod extending through the loop, wherein the tightening part is configured to tighten the flexible elongated member around the rod.

14. The system of claim 13, further comprising an additional rod secured adjacent the additional spacer by the tightening part.

15. The system of claim 12, wherein the tightening part comprises:
a passage, wherein the first portion and the second portion of the flexible elongated member extend from the spacer and through the passage of the tightening part; and
a tightener part configured to engage and immobilize the flexible elongated member in the passage.

16. The system of claim 15, wherein:
the first outlet is located in the first end;
the second outlet is located in the second end; and
the tightening part is located proximate the first end.

17. The system of claim 15, wherein the tightener part comprises a set screw.

18. The system of claim 12, wherein the tightening part comprises:
a body comprising:
a first lateral side positioned against the spacer;
a second lateral side positioned against the additional spacer; and
a medial surface connecting the first and second lateral sides;
wherein the passage extends from the first lateral side to the medial surface; and
wherein the additional passage extends from the second lateral side to the medial surface.

19. A vertebral fixing system, comprising:
a flexible elongated member having a first portion, a second portion, and an intermediate portion extending between the first portion and the second portion;
a spacer, wherein the flexible elongated member passes through the spacer;
a tightening part engaging the flexible elongated member, wherein the tightening part is configured to secure the flexible elongated member with respect to the spacer;
wherein one or both of the first portion of the flexible elongated member and the second portion of the flexible elongated member are configured to be wrapped around a bone and inserted into the tightening part, the tightening part configured to cinch the bone toward the tightening part using the flexible elongated member while the spacer maintains a distance between the bone and the tightening part by engaging the tightening part; and
wherein:
the spacer and an additional spacer are disposed on opposite sides of the tightening part;
the flexible elongated member extends through the spacer and the additional spacer; and
the tightening part is configured to draw the bone and an additional bone or rod toward each other and a center of the vertebral fixing system using the flexible elongated member.

\* \* \* \* \*